(12) United States Patent
Giedd et al.

(10) Patent No.: US 10,352,726 B2
(45) Date of Patent: Jul. 16, 2019

(54) THIN-FILM RESISTIVE-BASED SENSOR

(71) Applicant: Brewer Science Inc., Rolla, MO (US)

(72) Inventors: Ryan E. Giedd, Springfield, MO (US);
Vijaya Kayastha, Springfield, MO (US); Jonathan Fury, Springfield, MO (US); Robert Christian Cox, Rolla, MO (US)

(73) Assignee: Brewer Science, Inc., Rolla, MO (US)

( * ) Notice: Subject to any disclaimer, the term of this patent is extended or adjusted under 35 U.S.C. 154(b) by 554 days.

(21) Appl. No.: 14/806,238

(22) Filed: Jul. 22, 2015

(65) Prior Publication Data

US 2016/0025517 A1   Jan. 28, 2016

Related U.S. Application Data

(60) Provisional application No. 62/172,546, filed on Jun. 8, 2015, provisional application No. 62/027,753, filed on Jul. 22, 2014.

(51) Int. Cl.
  *G01D 5/16* (2006.01)
  *G01K 7/16* (2006.01)
  *G01N 27/12* (2006.01)

(52) U.S. Cl.
  CPC .............. *G01D 5/16* (2013.01); *G01K 7/16* (2013.01); *G01N 27/125* (2013.01); *G01N 27/127* (2013.01)

(58) Field of Classification Search
  CPC ...... G01D 5/16; G01N 27/125; G01N 27/127; G01K 7/16
  USPC .......................................................... 324/691
  See application file for complete search history.

(56) References Cited

U.S. PATENT DOCUMENTS

| | | | |
|---|---|---|---|
| 4,556,814 A | * | 12/1985 | Ito .......................... B06B 1/067 310/326 |
| 4,584,552 A | | 4/1986 | Suzuki et al. |
| 5,910,700 A | | 6/1999 | Crotzer |
| 6,463,789 B2 | | 10/2002 | Moos et al. |

(Continued)

FOREIGN PATENT DOCUMENTS

| | | |
|---|---|---|
| EP | 2230507 | 9/2010 |
| JP | 2008-170321 | 7/2008 |

(Continued)

OTHER PUBLICATIONS

Honeywell HIH-4000 Series, Humidity Sensors, Feb. 2010, 6 pages, http://sensing.honeywell.com/honeywell-sensing-hih4000-series-product-sheet-009017-5-en.pdf.

(Continued)

*Primary Examiner* — Farhana A Hoque
(74) *Attorney, Agent, or Firm* — Hovey Williams LLP

(57) ABSTRACT

Printed resistive-based sensors and transducers comprising a thin, electronically "active" sensing layer within a dielectric and/or metallic layered structure are provided. The electronic resistance of the active sensing layer is measured during a change in the sensor environment. By utilizing a multi-layered architecture around the active sensing layer, the electronic signal of the sensing element can be improved. By carefully selecting the architecture and materials that surround the active sensing layer, the sensitivity, stability, and selectivity of the sensor to detect changes in the environment are improved. This design allows for a number of specific application areas for environmental sensing.

19 Claims, 19 Drawing Sheets

(56) References Cited

U.S. PATENT DOCUMENTS

| | | | |
|---|---|---|---|
| 7,270,000 | B2 | 9/2007 | Nakada et al. |
| 8,252,237 | B2 | 8/2012 | Naito et al. |
| 8,759,153 | B2 | 6/2014 | Elian et al. |
| 9,006,796 | B2 | 4/2015 | Occhipinti |
| 9,006,891 | B2 | 4/2015 | Liang et al. |
| 9,007,593 | B2 | 4/2015 | Sailor et al. |
| 9,013,102 | B1 | 4/2015 | Wedding et al. |
| 9,017,867 | B2 | 4/2015 | Liu et al. |
| 9,018,060 | B2 | 4/2015 | Gryska et al. |
| 9,029,180 | B2 | 5/2015 | Britton et al. |
| 2004/0093928 | A1 | 5/2004 | DiMeo, Jr. et al. |
| 2006/0201247 | A1 | 9/2006 | Speldrich et al. |
| 2006/0213251 | A1 | 9/2006 | Rinzler et al. |
| 2006/0262457 | A1 | 11/2006 | Hirata et al. |
| 2007/0039385 | A1 | 2/2007 | Yang et al. |
| 2007/0114138 | A1 | 5/2007 | Krasteva et al. |
| 2008/0221806 | A1* | 9/2008 | Bryant ................. G01N 27/127 702/22 |
| 2011/0127446 | A1 | 6/2011 | Star et al. |
| 2011/0146398 | A1* | 6/2011 | Beck ................. G01F 1/6845 73/204.27 |
| 2011/0263036 | A1 | 10/2011 | Blauw et al. |
| 2012/0028820 | A1* | 2/2012 | Rhodes ................. B82Y 15/00 257/253 |
| 2013/0193417 | A1 | 8/2013 | Ponomarev et al. |
| 2014/0167791 | A1 | 6/2014 | Feyh et al. |
| 2014/0318990 | A1 | 10/2014 | Star |
| 2015/0023393 | A1 | 1/2015 | Britton et al. |

FOREIGN PATENT DOCUMENTS

| | | |
|---|---|---|
| JP | 2013-539040 | 10/2013 |
| WO | 2012/044419 | 4/2012 |
| WO | 2014/003979 | 1/2014 |

OTHER PUBLICATIONS

Sensirion SHT21S, Testing Guide for SHTxx Relative Humidity & Temperature Sensor Series, Version 1.2, May 2010, 4 pages, www.sensirion.com.

Texas Instruments HDC1000 Low Power, High Accuracy Digital Humidity Sensor with Temperature Sensor, Jul. 2014—Revised Jan. 2016, 31 pages, http://www.ti.com/lit/ds/symlink/hdc1000.pdf.

STMicroelectronics HTS221 Sensor, "Capacitive digital sensor for relative humidity and temperature," printed Oct. 1, 2017, 4 pages, http://www.st.com/web/catalog/sense_power/FM89/SC1718/PF260067.

Kim et al., "Hysteresis Caused by Water Molecules in Carbon Nanotube Field-Effect Transistors," Nano Letters, 2003, vol. 3, No. 2, pp. 193-198.

Ha et al., "Highly Stable Hysteresis-Free Carbon Nanotube Thin-Film Transistors by Fluorocarbon Polymer Encapsulation," Applied Materials & Interfaces, 2014, 6 (11), pp. 8441-8446.

Borini et al., "Ultrafast Graphene Oxide Humidity Sensors," ACS NANO, 2013, vol. 7, No. 12, 11166-11173.

Mogera et al., "Ultrafast response humidity sensor using supramolecular nanofibre and its application in monitoring breath humidity and flow," Scientific Reports 4, Article No. 4103 (2014), 9 pages.

International Search Report dated Nov. 16, 2015 in corresponding PCT/US2015/041577 filed Jul. 22, 2015.

International Preliminary Report on Patentability dated Feb. 2, 2017 in corresponding PCT/US2015/041577 filed Jul. 22, 2015.

Liu et at, "Humidity Sensitivity of Multi-Walled Carbon Nanotube Networks Deposited by Dielectrophoresis," Sensors, Mar. 11, 2009, vol. 9, 1714-1721.

Office Action in corresponding JP2017-503509 dispatched Feb. 5, 2019, 12 pages.

Office Action in corresponding EP15824262.8 dated Apr. 2, 2019, 2 pages.

* cited by examiner

THIN-FILM RESISTIVE-BASED SENSOR

RELATED APPLICATION

This application claims the priority benefit of U.S. Provisional Patent Application No. 62/027,753, entitled ULTRAFAST HUMIDITY DETECTOR FOR USE IN SPEECH AND HEALTH ANALYZERS, filed Jul. 22, 2014, and U.S. Provisional Patent Application No. 62/172,546, entitled THIN-FILM RESISTIVE-BASED SENSOR, filed Jun. 8, 2015, each of which is incorporated by reference herein.

BACKGROUND OF THE INVENTION

Field of the Invention

The present invention is broadly concerned with thin-film, resistive-based sensors.

Description of the Prior Art

Sensors able to detect environmental changes are in demand for a number of applications. Detection of changes in temperature, pressure, or various analytes in contact with the sensor (including moisture or gases in the air, etc.) is desirable for applications such as indoor and outdoor climate detection and control, process control, biometrics, medical uses, and much more. However, the usefulness of these sensors for various applications is limited by their ability not only to accurately and precisely measure stimuli, but their ability to detect and measure those stimuli in both the short and long term. Response time and settling time are very important specifications when trying to measure humidity for applications where immediate detection is necessary, such as breathing sensors. The response time of a sensor is the time it takes for a sensor to respond from no load to a step change in load. Settling time is the time it takes for a sensor to reach a stable output once it is turned on. Sensors must also be able to maintain long-term stability and measurement, and should demonstrate low hysteresis.

An environmental sensor can detect a physical change in the atmosphere, such as temperature, humidity, gas, or airflow. Through a sensing element, the sensor converts the variation through a transduction element into electrical signals that may be transmitted and measured. In many practices, the electronic resistance of the "active" layer is measured during a change in the sensor environment. If this measurement is single valued, stable, and reproducible, it can be calibrated and used as a signal indicative of the environment surrounding the sensor.

There are different approaches to the architecture and composition of environmental sensors. These approaches seek to increase one or more characteristics of efficient sensing capabilities: stability, sensitivity, low hysteresis, reliability, and/or accuracy. The most basic printed and/or thin film resistive-based sensors usually include a thin electronically "active" sensing layer printed on a dielectric substrate with a passivation or protection overlayer printed on the top surface.

Many prior art direct-current, resistive-based sensors have been plagued with poor performance as a result of very high hysteresis, low stability, and low accuracy. As these devices often utilize polymer-based materials or unpredictable materials, the problems of high hysteresis and low stability and accuracy are often attributed to the material choices used for the sensing element in the thin-film structure.

Other sensor technologies that are capacitance, inductive, optical, and physical-based and utilize established materials do not generally suffer from this type of poor performance. However, even though more reliable, these sensor technologies are slow.

SUMMARY OF THE INVENTION

The present invention provides a transducer comprising: a barrier layer; an active sensing layer in contact with at least two electrodes; and a dielectric layer between the active and barrier layers and having first and second sides. The at least two electrodes are both adjacent the dielectric layer second side, and the transducer is a resistive transducer.

The invention further provides a sensor comprising a transducer comprising: a barrier layer; an active sensing layer in contact with at least two electrodes; and a dielectric layer between the active and barrier layers and having first and second sides. The at least two electrodes are both adjacent the dielectric layer second side, and the transducer is a resistive transducer.

Finally, the invention provides a method of detecting the existence of a condition. The method comprises introducing a transducer into an environment where the analyte might be present. The tranducer comprises: a barrier layer; an active sensing layer in contact with at least two electrodes; and a dielectric layer between the active and barrier layers and having first and second sides. The at least two electrodes are both adjacent the dielectric layer second side. The method also comprises observing whether the transducer indicates the existence of the condition, where the existence is indicated by a change in resistance.

DETAILED DESCRIPTION OF THE PREFERRED EMBODIMENTS

The present invention is broadly concerned with novel transducers that can be incorporated into conventional sensor technology, as well as methods of using those transducers to detect the existence of a certain condition, such as a change in temperature or the presence of an analyte. Typical analytes that might be detected include those selected from the group consisting of humidity, gas, airflow, volatile organic compounds (VOCs such as amides, aldehydes, ethers, ketones, esters, and alcohols), and combinations of the foregoing. Advantageously, the present invention is particularly useful for detecting polar VOCs.

1. Embodiments of FIGS. 1-2

Figure 1:
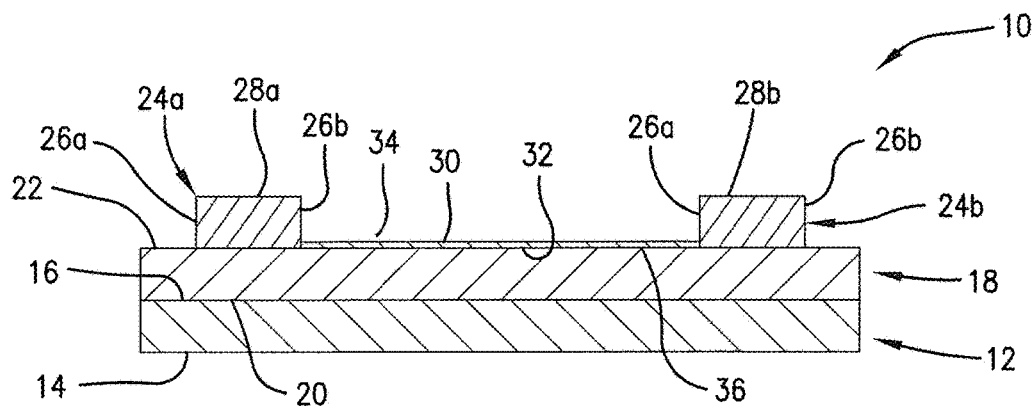
FIG. 1 is a schematic drawing showing one embodiment of the inventive transducer.
Figure 2:
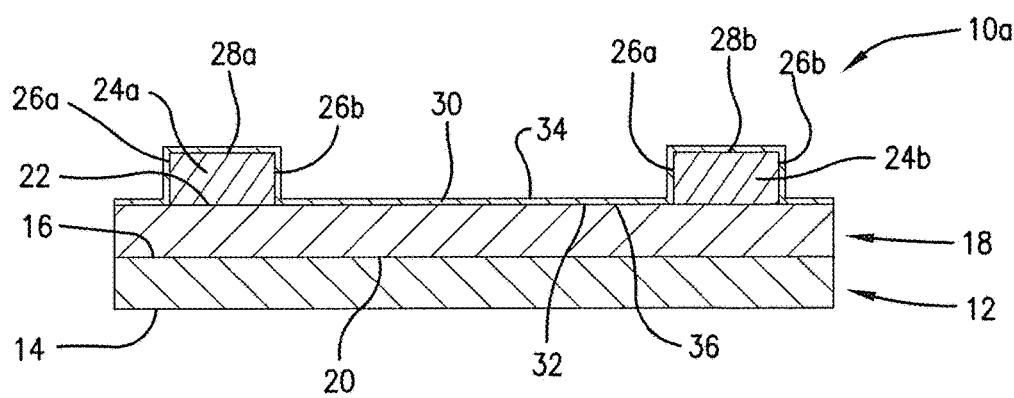
FIG. 2 is a schematic drawing showing a further embodiment of the inventive transducer, where the active sensing layer spans over and across the electrodes.

In more detail, and referring to FIG. 1, a first embodiment of a transducer according to the invention is shown. The transducer 10 comprises a barrier layer 12, having first and second sides 14, 16. Transducer 10 further comprises a dielectric layer 18, which is adjacent to barrier layer 12. Dielectric layer 18 has first and second sides 20, 22. As illustrated, first side 20 of dielectric layer 18 is preferably against second side 16 of barrier layer 12.

Transducer 10 also includes at least two electrodes 24a,b. Each electrode 24a,b has respective sidewalls 26a,b as well as respective upper surfaces 28a,b. Electrodes 24a,b rest on second side 22 of dielectric layer 18, while upper surfaces 28a,b are remote from second side 22. Transducer 10 additionally includes an active sensing layer 30, which has a first side 32 and a second side 34. Active sensing layer 30 is adjacent dielectric layer 18 and, as illustrated, first side 32 of active sensing layer 30 is preferably in contact with second side 22 of dielectric layer 18, forming interface 36.

Importantly, active sensing layer 30 is also in contact with each electrodes 24a,b. Referring to FIG. 1, it is noted that active sensing layer 30 is touching sidewall 26b of electrode 24a, as well as sidewall 26a of electrode 24b. In another embodiment, active sensing layer 30 conforms to electrodes 24a,b. That is, active sensing layer 30 contacts the respective sidewalls 26a,b and upper surfaces 28a,b of electrodes 24a,b (see transducer 10a of FIG. 2). In another embodiment, the electrodes 24a,b may be positioned on top of the active sensing layer 30 rather than under the active sensing layer 30 (i.e., their order could be "flipped"), provided contact is still achieved. Thus, any arrangement that results in active sensing layer 30 contacting both electrodes 24a,b is acceptable.

Barrier Layer 12

Barrier layer 12 as shown in the figures functions as an isolation layer. Barrier layer 12 is designed to isolate the active (i.e., sensing) layer 30 from the chemical and physical properties of any substrate that might be present (see below), as well as to prevent environmental stimuli from affecting active sensing layer 30. The material and properties of the barrier layer 12 depend upon the type of transducer being fabricated. The barrier layer 12 may be, but is not limited to, a metal, ceramic, polymer, composite, or a mixture thereof. The layer 12 may be conductive or electrically insulating. Furthermore, barrier layer 12 may be deposited by any suitable technique, including those selected from the group consisting of screen printing, spray coating, Aerosol Jet® printing, ink-jet printing, flexographic printing, gravure printing, lithographic techniques, spin coating, evaporation, sputtering, lamination, ALD, CVD, and PECVD. The average thickness of the barrier layer 12 is preferably from about 50 nm to about 50 μm, more preferably from about 100 nm to about 4 μm, and even more preferably from about 100 nm to about 2 μm.

When the transducer is an analyte transducer, the barrier layer 12 should not react chemically or physically with the analyte. Thus, it is preferred that the barrier layer 12 have an analyte solubility of less than about 0.02%, preferably less than about 0.001%, and more preferably about 0, as measured by ASTM method D-570. The diffusion rate of analyte through the barrier layer 12 should be less than about 1 g/m$^2$/day, preferably less than about 0.01 g/m$^2$/day, and more preferably about 0.001 g/m$^2$/day, as measured by ASTM method F1249. For a humidity transducer, the barrier layer 12 is preferably hydrophobic, and does not allow water vapor to remain in the transducer structure or pass either direction therethrough.

Dielectric Layer 18

Dielectric layer 18, as illustrated in the figures, functions as a signal enhancement layer, and is located between the transducer electrodes 24a,b and the barrier layer 12. Changing the material from which dielectric layer 18 is formed can greatly increase the signal-to-noise ratio of the output signal from the transducer 10. The dielectric layer 18 preferably has a conductivity of less than about $10^{-11}$ S/m, more preferably less than about $10^{-21}$ S/m, and even more preferably from about $10^{-25}$ S/m to about $10^{-23}$ S/m. The sheet resistance of the dielectric layer 18 should be at least about $10^{16} \Omega/\square$, preferably at least about $10^{26} \Omega/\square$, and more preferably from about $10^{29} \Omega/\square$ to about $10^{31} \Omega/\square$. The dielectric layer 18 may be deposited by any suitable technique, including those selected from the group consisting of screen printing, spray coating, Aerosol Jet® printing, ink-jet printing, flexographic printing, gravure printing, drawbar coating, dip coating, lithographic techniques, spin coating, evaporation, sputtering, lamination, ALD, CVD, and PECVD.

The average thickness of the dielectric layer 18 is preferably from about 1 µm to about 10 µm, more preferably from about 1 µm to about 8 µm, and even more preferably from about 1 µm to about 3 µm. In embodiments where a conductive barrier layer 12 is used, the dielectric layer 18 should have substantially no pinholes, and preferably no pinholes.

In one embodiment, the dielectric layer 18 may react with the detected condition or stimulus. For instance, in an analyte transducer, the dielectric layer 18 may experience a chemical or physical change or reaction when contacted by the analyte. This chemical or physical change or reaction can further enhance or amplify the output signal from the active sensing layer 30 upon exposure to the analyte. For example, if the dielectric layer 18 is made out of a material that is soluble in alcohol, the device not only responds to the alcohol diffusing through the active sensing layer, but also to the morphological changes in the dielectric layer 18, greatly increasing overall sensitivity. In this case, reversible reactions in the dielectric layer 18 are preferred over irreversible reactions, because irreversible reactions in the dielectric layer 18 are a primary cause for hysteresis within a transducer.

When the dielectric layer 18 is reactive, it should have a diffusion rate for the analyte of at least about 50 g/m²/day, preferably at least about 500 g/m²/day, and more preferably from about 2000 g/m²/day to about 5000 g/m²/day, as measured by ASTM method F1249. When the dielectric layer 18 is reactive, it should have an analyte solubility in the layer of at least about 0.8% preferably at least about 2.0%, and more preferably from about 5.0% to about 20%, as measured by ASTM method D-570. The dielectric layer 18 can be made of any non-conductive material or materials, including those selected from the group consisting of polymers (such as polyesters and polymethylmethacrylate (PMMA)), photoresists, ceramics, metal composites, metal oxides, and mixtures thereof; and depends upon the analyte of interest.

In another embodiment, the dielectric layer 18 does not react with the detected stimulus. In this case, the dielectric layer 18 should not experience a chemical or physical change or reaction when contacted by the analyte. In this way, the dielectric layer 18 may behave as an isolation layer, isolating the substrate (if present; see below) or barrier layer 12 from environmental signals, and/or isolating the active sensing layer 30 from substrate and/or barrier layer 12 effects. When the dielectric layer 18 is nonreactive, it should have a diffusion rate for the analyte of less than about 4 g/m²/day, preferably less than about 1 g/m²/day, and more preferably from about 0 g/m²/day to about 0.001 g/m²/day, as measured by ASTM method F1249. When the dielectric layer 18 is nonreactive, it should have an analyte solubility in the layer of less than about 0.02%, preferably less than about 0.001%, and more preferably about 0%, as measured by ASTM method D-570. The nonreactive dielectric layer 18 can be made of any non-conductive material or materials, including those selected from the group consisting of polymers (such as polytetrafluoroethylene [PTFE] silicone dielectric materials, cycloolefin copolymers, polyvinylidene fluoride [PVDF], and polystyrene), photoresists, ceramics, metal nitrides (such as silicon nitride), metal oxides (such as aluminum oxide), metal composites, and combinations of the foregoing.

Electrodes 24a,b

Electrodes 24a,b are preferably planar electrodes, but could also be an inter-digitated electrodes. Preferably, the electrodes 24a,b have high electron or hole mobilities and large carrier concentrations. Suitable materials for forming electrodes 24a,b include those selected from the group consisting of silver, poly(3,4-ethylenedioxythiophene) (PEDOT), gold, highly-doped silicon, conductive carbon nanotubes (CNTs), and graphene inks, palladium, copper, aluminum, any conductive polymer, and CNT/graphene-conductive polymer composites. The preferred materials have a low Schottky barrier and low contact resistance to the active sensing layer 30.

The electrode may be formed by any suitable technique, including those selected from the group consisting of screen printing, spray coating, Aerosol Jet® printing, ink-jet printing, flexographic printing, gravure printing, lithographic techniques, spin coating, evaporation, sputtering, and laser ablation.

Active Sensing Layer 30

Active sensing layer 30 provides an electronic resistance signal that changes proportionally to environmental change. Any material that responds to the target environmental change with a change in its electronic resistance may be used in the active sensing layer 30. This change in electronic resistance may be the result of a change in its electronic structure, defect state, or electronic carrier density. Preferably, the resistance of the active sensing layer 30 is from about 5 kΩ to about 10 MΩ, more preferably from about 100 kΩ to about 5 MΩ, even more preferably from about 500 kΩ to about 2 MΩ. Upon exposure to an environmental stimulus, the resistance of the active sensing layer 30 should change proportionally to the change in environmental stimulus. Preferably the change in resistance should result in an output signal change of at least about 0.1% per ° C. or % RH change, and more preferably at least about 0.5% per ° C. or % RH change (for temperature and relative humidity transducers, respectively).

Preferably, the material used to form the active sensing layer 30 is a planar material that can be provided as a film or fabric, as opposed to a wire, narrow bridge, rod, individual CNTs, or the like. Additionally, active sensing layer 30 comprises a disordered conductor with a large number of defect states and a sheet or film morphology giving rise to irregular conduction paths. This disorder or irregularity leads to "junctions" among the particular component being utilized, and these junctions are important for the proper functioning of the active sensing layer 30. Suitable materials for the active sensing layer include those selected from the group consisting of carbon nanotubes (metallic or semiconducting), a functionalized or non-functionalized carbon nanotube (CNT) fabric, amorphous carbon film, pyrolytic carbon, graphite, graphene, carbon fiber, fullerenes carbon soot, carbon black, silicon, ion-implanted and other conductive polymers (such as PEDOT:PSS, polyanilines, polyfluorenes, polyphenylenes, polypyrenes, polyazulenes, polynaphthalenes, polypyrroles, polycarbazoles, polyindoles, polyazepines, polyacetylenes, polyphenylenevinylenes, and polythiophenes), metal-particle-doped CNTs or graphene and composites and mixtures thereof. When the active sensing layer 30 is formed from CNTs, the junctions noted above are created between tubes. In conductive polymers, highly conductive crystalline regions and low-conductivity amorphous regions cooperate to form the junctions. In other materials, the are "plates" within the material that cooperate to form the junctions in the sheet or fabric of active sensing layer 30.

The active sensing layer 30 is selected to be very thin, like a very thin "skin," approaching a 2-dimensional sheet or film. Thus, active sensing layer 30 should have an average thickness that is less than about 1000 nm, preferably less than about 200 nm, more preferably less than about 100 nm, and even more preferably from about 10 nm and to about 100 nm. In a particularly preferred embodiment, the active sensing layer 30 has an average thickness of less than about 30 nm, and preferably from about 1 nm to about 30 nm. At such low thicknesses, active sensing layer 30 has negligible bulk properties such as mass, volume, and heat capacity. Therefore, this active sensing layer 30 takes on many of the chemical, physical, and biological characteristics of the surrounding layers, thus making the selection of dielectric layer 18 important for the particular target or condition to be sensed.

The active sensing layer 30 may be deposited by any suitable technique, including those selected from the group consisting of screen printing, spray coating, Aerosol Jet® printing, ink-jet printing, dip coating, airbrush techniques, flexographic printing, gravure printing, lithographic techniques, spin coating, evaporation, sputtering, lamination, ALD, CVD, and PECVD.

Interface 36

The interface 36 between the dielectric layer 18 and the active sensing layer 30 is considered a "choke region." The interface 36 is not a separate material or discrete layer, but the properties of the interface 36 can be modified by changing the nature of the interface 36. In some embodiments, the choke region/interface 36 operates to reflect some of the incoming environmental signal back into the active sensing layer 30. In other embodiments, the interface 36 may be altered by treating one or both of the first side 32 of active sensing layer 30 and second side 22 of dielectric layer 18, such as by heat treatment, radiation, fluorination, UV curing, or ion implantation.

2. Embodiment of FIG. 3

This and the following embodiments provide situations where additional layers are present. These layers could be added to the embodiments of either of FIG. 1 or 2, however, for simplicity's sake, they are illustrated with the embodiment of FIG. 2. Similar numbers to the FIGS. 1 and 2 embodiment represent similar parts, and references is made to that discussion above, rather than repeating it with each embodiment.

Figure 3:
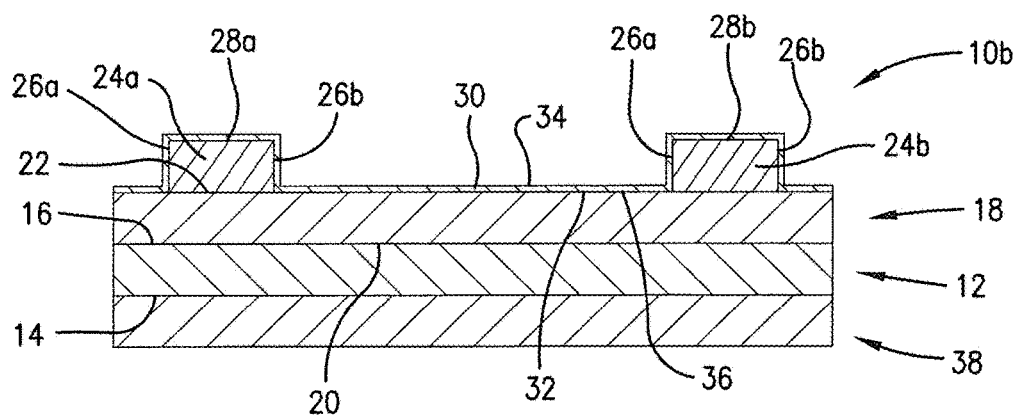
FIG. 3 is a schematic illustration of another embodiment of the inventive transducer, where the transducer is supported on a substrate.

Referring to FIG. 3, a transducer 10b is illustrated. Transducer 10b differs from previous embodiments in that it further comprises a substrate 38 against first side 14 of barrier layer 12. The substrate 38 may be formed from any number of materials, including those selected from the group consisting of metals, polymers, ceramics, silicon, or single crystal. Preferably, the material is selected from the group comprising metals, metal oxides, metal nitrides, semiconductors, glass, paper, and organic polymers. Suitable metals include those selected from the group consisting of silicon, aluminum, and stainless steel. Suitable metal oxides include those selected from the group consisting of aluminum oxides and silicon oxides. Suitable metal nitrides include those selected from the group consisting of silicon nitride and tin nitride. Suitable organic polymers include those selected from the group consisting of polyimides (such as Kapton® film), polyamides, polysulfones, poly ether sulfones, polyether ether ketone (PEEK), polyethylene terpthalate (PET), polytetrafluoroethylene (PTFE, such as Teflon), acrylates, methacrylates, styrenics, cycloolefin polymers (such as Zeonor), cycloolefin copolymers, polyesters, and polyethylene naphthalates. The substrate may be electrically conducting, insulating, flexible, or rigid.

3. Embodiment of FIG. 4

Figure 4:
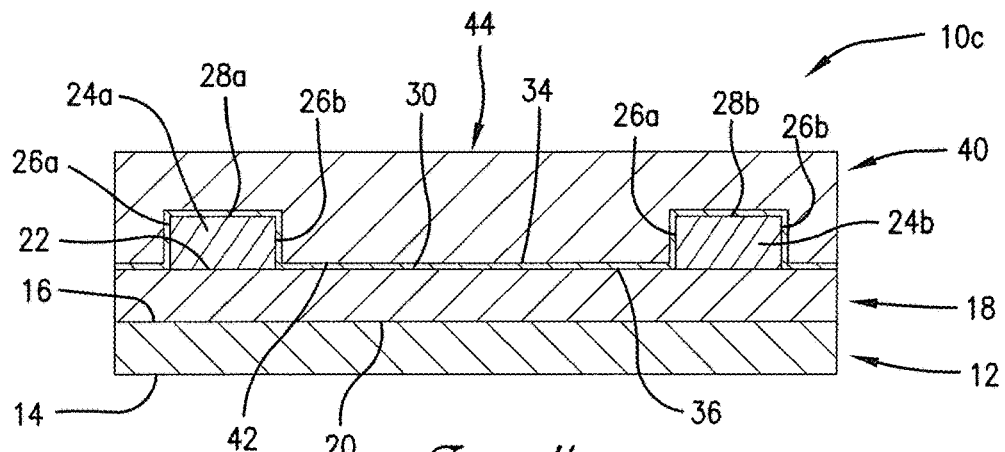
FIG. 4 is a schematic illustration showing a further embodiment where a signal enhancement layer is on the active sensing layer.

Referring to FIG. 4, a further embodiment is illustrated in the form of transducer 10c. Transducer 10c is similar to that shown in FIG. 2, except that it further comprises a signal enhancement layer 40. Signal enhancement layer 40 has a first side 42 and a second side 44. First side 42 of signal enhancement layer 40 is adjacent to all or part of active sensing layer 30, and preferably against second side 34 of active sensing layer 30.

Signal enhancement layer 40 is preferably a dielectric material. That is, signal enhancement layer 40 preferably has a conductivity of less than about $10^{-11}$ S/m, more preferably less than about $10^{-21}$ S/m, and even more preferably from about $10^{-25}$ S/m to about $10^{-23}$ S/m. The sheet resistance of the signal enhancement layer 40 should be at least about $10^{16} \Omega/\square$, preferably at least about $10^{26} \Omega/\square$, and more preferably from about $10^{29} \Omega/\square$ to about $10^{31} \Omega/\square$. The signal enhancement layer 40 may be deposited by any suitable technique, including those selected from the group consisting of screen printing, spray coating, Aerosol Jet® printing, ink-jet printing, flexographic printing, gravure printing, drawbar coating, dip coating, lithographic techniques, spin coating, evaporation, sputtering, lamination, ALD, CVD, and PECVD. The thickness of the signal enhancement layer 40 is preferably from about 50 nm to about 50 µm, more preferably from about 100 nm to about 4 µm, and even more preferably from about 100 nm to about 2 µm. The signal enhancement layer 40 should have a diffusion rate for the analyte of at least about 50 g/m²/day, preferably at least about 500 g/m²/day, and more preferably from about 2000 g/m²/day to about 5000 g/m²/day, as measured by ASTM method F1249. In this embodiment, the signal enhancement layer 40 preferably has a diffusion rate for non-analytes of less than about 1 g/m²/day, more preferably less than about 0.01 g/m²/day, and even more preferably from about 0 g/m²/day to about 0.001 g/m²/day, as measured by ASTM method D-570.

In one embodiment, the signal enhancement layer 40 may react with the detected stimulus. For instance, in an analyte transducer, the signal enhancement layer 40 may experience a chemical or physical change or reaction when contacted by the target analyte. This chemical or physical change or reaction can further enhance or amplify the output signal from the active sensing layer 30 upon exposure to the analyte. When the signal enhancement layer 40 is reactive, it should have an analyte solubility in the layer of at least about 0.8%, preferably at least about 2.0%, and more preferably from about 5.0% to about 10%, as measured by ASTM method D-570. The reactive signal enhancement layer 40 can be made of any non-conductive material or materials, including those selected from the group consisting of polymers (such as polyesters or polymethylmethacrylate [PMMA]), photoresists, ceramics, or metal composites, or mixtures thereof.

In another embodiment, the signal enhancement layer 40 preferably does not react with the detected stimulus. In this case, the signal enhancement layer 40 should not experience a chemical or physical change or reaction when contacted by the analyte. In this way, the signal enhancement layer 40 may behave as an isolation layer, isolating the active sensing layer 30 from deleterious environmental effects. When the signal enhancement layer 40 is nonreactive, it should have an analyte solubility in the layer of less than about 0.02%, preferably less than about 0.001%, and more preferably about 0%, as measured by ASTM method D-570. The nonreactive signal enhancement layer 40 can be made of any non-conductive material or materials, including those selected from the group consisting of polymers (such as polytetrafluoroethylene [PTFE], silicone dielectric materials, cyclicolefin copolymers, polyvinylidene fluoride [PVDF], and polystyrene), photoresists, ceramics, or metal composites, metal oxides, metal nitrides (such as silicon nitride), or mixtures thereof.

4. Embodiments of FIGS. 5-6

Figure 5:
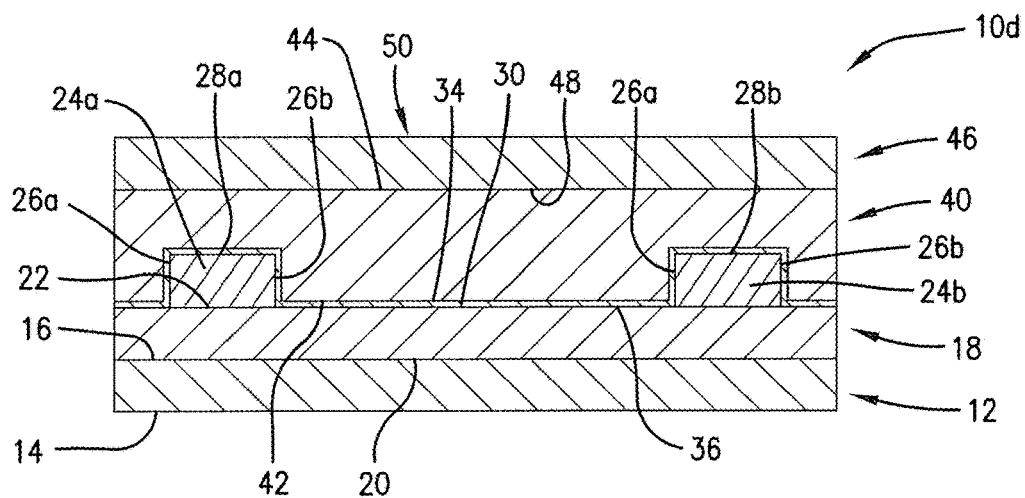
FIG. 5 is yet another embodiment showing a transducer similar to that of FIG. 4, but with a filter layer adjacent the signal enhancement layer.

Referring to FIG. 5, a transducer 10d is illustrated. Transducer 10d is similar to the transducer 10c of FIG. 4, except that transducer 10d further comprises a filter layer 46. Filter layer 46 comprises first and second sides 48, 50, and is located adjacent to the signal enhancement layer 40, and preferably first side 48 is against second side 44 of signal enhancement layer 40.

Figure 6:
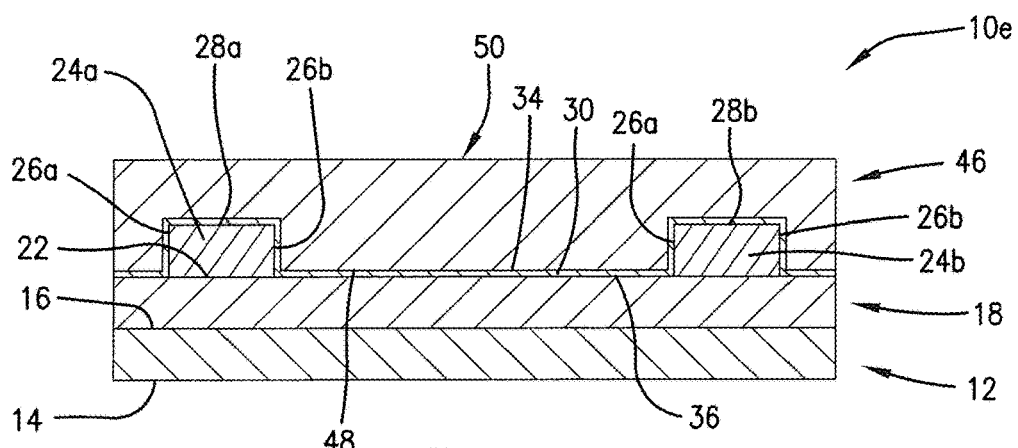
FIG. 6 is a schematic drawing of another embodiment showing a transducer similar to that of FIG. 5, but with a filter layer adjacent the active sensing layer.

In a further embodiment illustrated as transducer 10e of FIG. 6, a signal enhancement layer 40 is not present, thus first side 48 of filter layer 46 is adjacent active sensing layer 30. More preferably, first side 48 of filter layer 46 is against second side 34 of active sensing layer 30 in this embodiment.

Regardless of whether referencing transducer 10d or 10e, the filter layer 46 is located between some or all of the transducer electrodes 24a,b and the environment. The filter layer 46 is designed to isolate the active sensing layer 30 from some or all environmental stimuli. That is, the filter layer 46 may enhance the function or selectivity of the transducer by allowing only the desired environmental signal to contact and react with the active sensing layer 30. The material and properties of the filter layer 46 depend upon the type of transducer being fabricated. The filter layer 46 is preferably formed from a material selected from the group consisting of metal films, polymeric films, ceramic films, single crystal films, ion-selective films, chemical-selective films, biological-selective films, metal oxide films, metal nitride films, organometallic films, and combinations of the foregoing.

The filter layer 46 may be conductive or electrically insulating. Furthermore, the filter layer 46 may be deposited by any suitable technique, including those selected from the group consisting of screen printing, spray coating, Aerosol Jet® printing, ink-jet printing, flexographic printing, gravure printing, drawbar coating, dip coating, lithographic techniques, spin coating, evaporation, sputtering, lamination, laser ablation, ALD, CVD, and PECVD. The thickness of the filter layer 46 is preferably from about 10 nm to about 150 μm, more preferably from about 50 nm to about 100 μm, and even more preferably from about 100 nm to about 2 μm.

In one embodiment, when the transducer 10d or 10e is an analyte transducer, the filter layer 46 preferentially allows the desired analyte to pass therethrough, while blocking any undesired environmental signals. Preferably, the filter layer 46 should have a high analyte transmission rate and a low analyte absorption and reflection rate. The filter layer 46 should have a diffusion rate for the analyte of at least about 50 $g/m^2/day$, preferably at least about 500 $g/m^2/day$, and more preferably from about 2000 $g/m^2/day$ to about 5000 $g/m^2/day$, as measured by ASTM method F1249. For instance, for a humidity transducer, filter layer 46 is a water-permeable membrane of a material, such as those selected from the group consisting of paper, cellulose paper, GoreTex materials, PVDF, and PTFE, and any porous, moisture-permeable layer.

In another embodiment, when the transducer 10d or 10e is intended to detect physical stimuli such as temperature or force, and effects from concentrations of analytes in the environment are not desired, the filter layer 46 is preferably an encapsulant that prevents any analytes, such as moisture or chemicals, from penetrating the filter layer 46. For example, with a temperature transducer, the filter layer 46 would be an encapsulant with high thermal conductivity that prevents any environmental signal except heat from interacting with the active sensing layer. In this case, preferred materials for the filter layer 46 include those selected from the group consisting of metals, metal oxides (such as aluminum oxide or beryllium oxide), metal nitrides, crystalline non-metal (such as diamond or quartz), silicones, polyacrylates, polymethacrylates, polyurethanes, polysaccharides, and styrenics. For non-analytes, the filter layer 46 should have a diffusion rate with respect to non-analytes of less than about 1 $g/m^2/day$, preferably less than about 0.01 $g/m^2/day$, and more preferably less than about 0.001 $g/m^2/day$, as measured by ASTM method F1249. Where the transducer 10d or 10e is a temperature transducer, the filter layer 46 should have a thermal conductivity of at least about 10 W/m·K, preferably at least about 100 W/m·K, and more preferably at least about 400 W/m·K.

Formation

Advantageously, the manufacturing of the inventive transducer can be accomplished by printed electronics technology. The use of printing techniques to manufacture the sensors is desirable because of lower cost, higher speed, and versatility of substrates and form factors. However, it will be appreciated that the sensor could be manufactured using standard photolithography techniques and materials, if the materials and dimensions of the sensor are selected appropriately.

In one embodiment, the transducer is packaged into a device (e.g., sensor) comprising a transducer and a controller unit. The controller unit is able to interpret the change in resistance of the transducer, and to calculate the concentration of environmental stimulus based on the change in resistance across the transducer. As mentioned above, the device may optionally include a temperature sensor to compensate for temperature fluctuations in and around the device.

In one embodiment, the device comprises an electronics and software readout and analysis system capable of amplifying the signal from the transducer with sufficient band pass to measure the high-speed electrical resistance fluctuations produced by the sensor. These signals, once amplified, are converted to digital signals for subsequent data analysis in a controller unit, such as a microcontroller, microprocessor, or logic array system.

The controller unit preferably comprises a hardware section including amplifier and signal conditioning circuits with or without hardware filtering or analog or digital signal processing stages, followed by a digital conversion into a microprocessor, microcontroller, or logic array for further signal analysis, storage, and visible presentation of results. In other words, the inventive transducers can be incorporated into conventional sensors and other devices requiring a transducer by following conventional processes.

Applications

When utilizing the inventive transducer as a humidity, gas, or VOC sensor, the resistance of the active sensing layer is also slightly temperature dependent. Optionally, for greater precision, a hermetically sealed temperature sensor can be used as a temperature compensator element to be integrated with the humidity, gas, or VOC sensor. This temperature compensator element can be incorporated directly onto the device structure or in a separate structure. Since the compensator element is hermetically sealed, the compensator element is only sensitive to temperature and can be used in a subtraction mode to eliminate the effect of temperature on the overall humidity, gas, or VOC sensor signals.

When the inventive transducer is used to create a humidity sensor, the humidity transducer preferably has an equilibrium time of less than about 5 msec, more preferably less than about 1.0 msec, and even more preferably from about 0.5 msec to about 1.0 msec. The humidity transducer also has very low response times. The humidity transducer should have a response (or rise) time of less than about 50 msec, preferably less than about 20 msec, more preferably less than about 10 msec, and even more preferably from about 5 msec to about 10 msec under atmospheric conditions. The humidity transducer has a fall time of less than about 100 msec, preferably less than about 90 msec, more preferably less than about 50 msec, and even more preferably from about 20 msec to about 50 msec under atmospheric conditions.

The humidity transducer is based on a changing resistance associated with a surface humidity change within the electrode structure. Preferred changes are at least a resistance change of 20% at room temperature with a 30% change in humidity. The current required for the sensor is preferably from about 500 nA to about 20 µA, more preferably from about 500 pA to about 200 nA, even more preferably from about 50 pA to about 200 pA.

Figure 7:
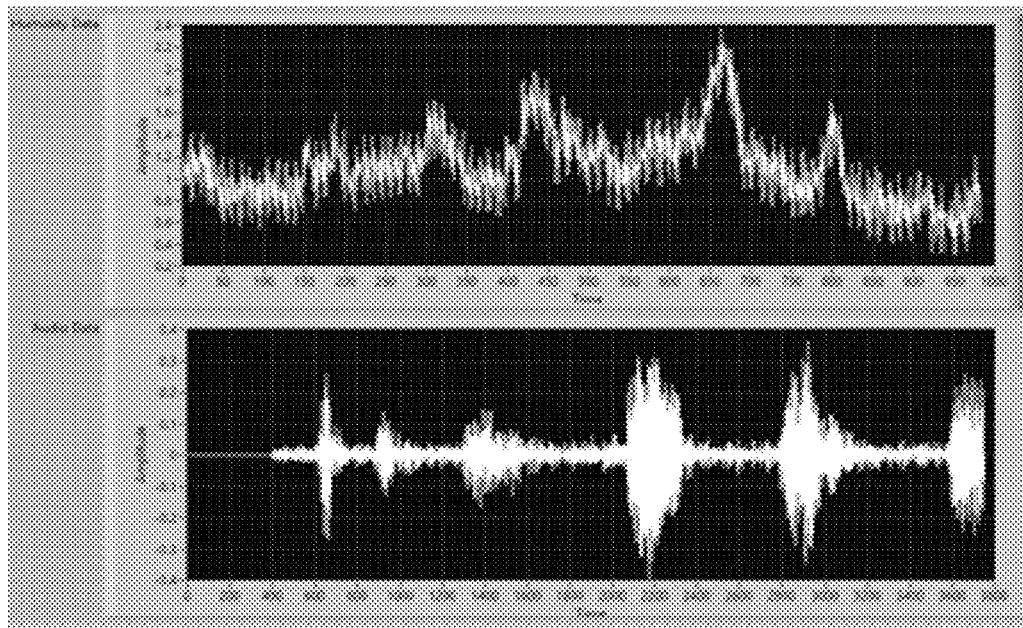
FIG. 7 is a graph showing the humidity and audio signal while speaking "testing, one, two, three"

The speed of the transducers can facilitate a number of applications, such as speech detection and recognition. For example, FIG. 7 shows the simultaneous humidity signal from one of the transducers (top panel) and a simultaneous audio signal (bottom panel) when speaking the phrase "testing, one, two, three." Each syllable has a unique humidity signature and coupled with the audio signal can indicate the hydration of the speaker through amplitude information and the identity of the speaker by frequency information.

A volatile level sensor can be created by utilizing the high speed of the transducer. In one embodiment, the transducer and related electronics can be used to turn on and off a light when the polar solvent concentration exceeds or goes below a pre-determined set point level. In the this way, dryers may be controlled or turned off when the polar solvent vapor emanating from the object drops below levels where the contents of the dryer are expected to be dry.

Performance of Transducers

Figure 8:
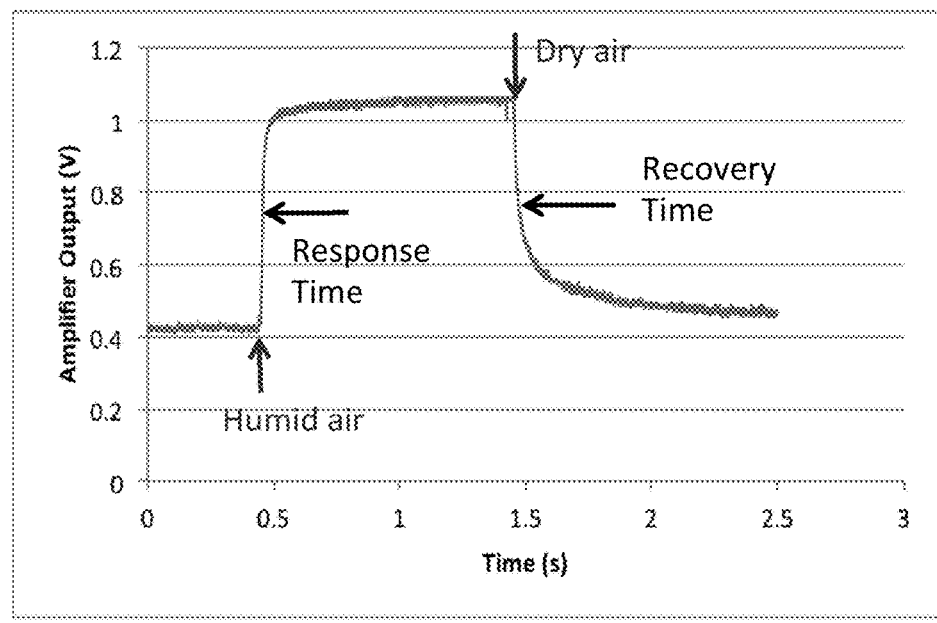
FIG. 8 is a graph showing the response of a transducer to 1-second pulse of humid air.

FIG. 8 shows the behavior of a specific basic sensor when exposed to a one-second pulse of increased relative humidity (RH). The transducer reacts and recovers quickly, within 100 ms. At these speeds, the choke region formed at the interface between a CNT-based active sensing layer and a PET signal enhancement layer dominates. These humidity transducers have ultrafast response times of less than 10 ms and a recovery time of about 40 ms. Very similar behavior was observed for fast pulses of other constituents including alcohol and ketones, with the primary differences being in exact response and recovery times, but they were all within 250 ms.

Figure 9:
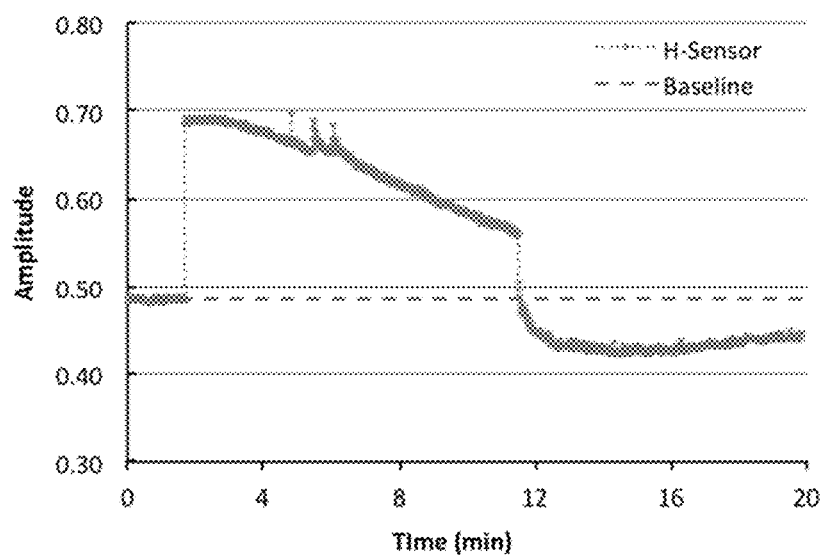
FIG. 9 is a graph depicting the response of the same transducer as shown in FIG. 8 to 10-minute pulse of humid air

FIG. 9 shows the response of the same basic transducer when exposed to higher relative humidity for an extended time (10 minutes). During this longer time, the choke region does not completely block the diffusion of water into the signal enhancement layer. This effect slows the recovery time of the sensor, as the humidity that diffused into the signal enhancement layer must now flow out before the sensor can fully recover to its equilibrium condition. This is hysteresis of the device caused by signal enhancement layer or dielectric layer and not the active layer.

Figure 10:
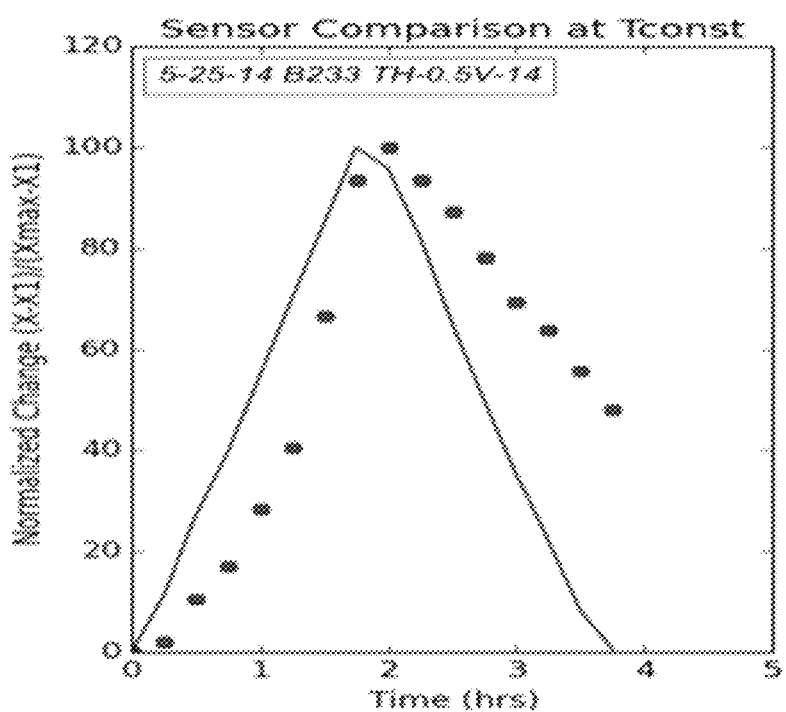
FIG. 10 is a graph of the response of a transducer to a slowly varying humidity concentration.

In FIG. 10, the relative humidity was varied slowly in the form of a triangular wave with a period of about 4 hours in a sealed environmental chamber and the resulting signal from the same transducer from FIGS. 8 and 9 is shown. The line in the figure shows the input concentration variation with time, while the dots show the readings from the humidity transducer. When exposed to the much slower variation in concentration, the sensor active cannot come to equilibrium even after many hours.

The response in FIG. 10 shows that the sensor reacts relatively quickly at the peak to the changing environmental concentration of water vapor. This is a region of higher concentration change frequency, and the transducer acts like a high-pass filter and responds faster to this concentration fluctuation.

Calculation of Transducer Hysteresis

As one environmental stimulus is ramped up and back down, current output from the transducers are recorded at a fixed applied voltage. The current output values are converted into resistance values using the equation:

Resistance=(Applied Voltage)/(Current Output)

A graph of resistance output vs. temperature is plotted, and a best-fit line is drawn. Using slope and y-intercept values of the best-fit line, each resistance value at each recorded data point of the forward and reverse cycle, as measured by a calibrated reference is converted into the calculated temperature values using the following equation:

$$X_{cal}=((R-c))/m$$

where 'R' is the resistance output, 'c' is the y-intercept of the best-fit line, 'm' is the slope of the best-fit line, and 'Xcal' is the calculated value. At each actual recorded data point, the difference between the calculated value from the actual data point during forward and reverse cycles is calculated. The differences at each recorded data point during forward and reverse cycles is added. This is done for each data point. The maximum deviation of calculated value from actual value in the entire range is taken as hysteresis of the device.

Calculation of Temperature Sensor Accuracy

In order to calculate the accuracy of the transducer, the difference between the actual and calculated value as calculated above is found for a cycle of a given stimulus. The accuracy of the transducer is calculated as the largest difference between the calculated and actual values for that transducer.

EXAMPLES

The following examples set forth preferred methods in accordance with the invention. It is to be understood, however, that these examples are provided by way of illustration and nothing therein should be taken as a limitation upon the overall scope of the invention.

Example 1

Preparation of Carbon Nanotube Ink 1

Brewer Science® CNTRENE® 1020 material was used as the source for CNT ink. To facilitate printing, a 1:1 solution of dimethylformamide (DMF) (Sigma-Aldrich, Part #D158550-4L) and deionized water was used to dilute the ink to an optical density of 2.0 for spraying onto the devices by diluting the original CNT ink (equivalent OD of 24) by about 1:12 with the DMF and DI water solution and shaking for about 30 seconds.

Example 2

Preparation of Carbon Nanotube Ink 2

Brewer Science® CNTRENE® 1020 material was used as the source for CNT ink. To facilitate printing, deionized water was used to dilute the ink to an optical density of 2.0 for spraying onto the devices by diluting the original CNT ink (equivalent OD of 24) with DI water and shaking for about 30 seconds.

Example 3

Fabrication of Integrated Temperature/Analyte Transducers on PET

Figure 11:
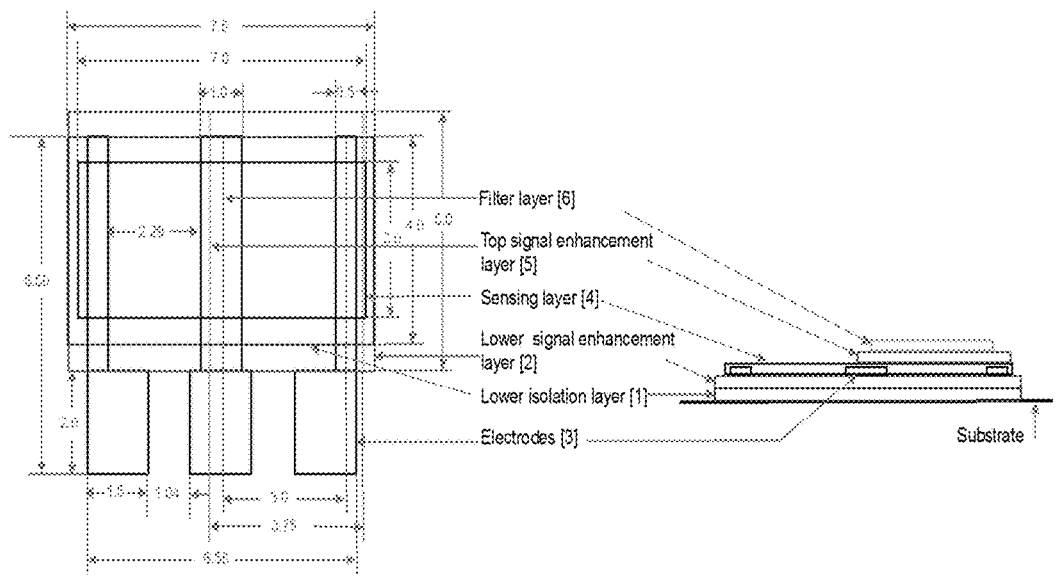
FIG. 11 is a top and side view of the integrated temperature and analyte transducer of Example 3.

In this Example, 32 integrated temperature/analyte transducers were fabricated on a flexible Melinex® ST730 PET substrate (Tekra, Inc., 16700 West Lincoln Avenue, New Berlin, Wis. 53151. The structure of the transducers is shown in FIG. 11. First, the substrate was baked in a conveyor oven at 130° C. at a 10"/min speed. Next, a bottom metal layer, AG-800 silver conductive ink (Conductive Compounds, Hudson, N.H.), was screen printed onto the substrate using a AT-60PD screen printer using the following parameters: screen: polyester, 230 threads/inch, flood/squeegee speed: 225 mm/s, flood bar pressure: 10 psi, squeegee pressure: 25 psi. The substrate was then cured in the conveyor oven at 130° C. at a 10"/min speed. The cured silver film had a thickness of 5 µm. A bottom insulation layer, an experimental cycloolefin polymer from Brewer Science, Inc., was screen printed on top of the metal layer using the same parameters as the metal layer and cured in the conveyor oven at 130° C. at a 10"/min speed. The film thickness was about 8 µm. The silver electrodes were then screen printed on top of the bottom insulation layer using the same screen printing and curing parameters as the metal layer. The material from Example 1 was then spray coated across the electrode region using a custom-built spray coater with Sono-Tek spray head with a platen temperature of 135° C., a scan width of 2 mm, a flow rate of 10 ml/hr, scan speed of 60 mm/s, and a Sono-Tek model 048-00214 spray head. The CNT film thickness was approximately 20 nm. A top insulation layer, the same material as the bottom insulation layer, was screen printed over the CNTs on temperature transducer region using the same screen printing parameters and cured in the conveyor oven at 130° C. at a 10"/min speed, and was further UV-cured using LC-6B Benchtop Conveyor from Fusion UV Systems, Inc., at conveyor speed of 52"/min. Finally, a top metal layer, AG-800 silver conductive ink, was screen printed onto the temperature transducer using the same screen printing parameters as the bottom metal layer and cured in the conveyor oven at 130° C. at a 10"/min speed. The film thicknesses and the screen printing parameters for these top layers were the same as respective bottom layers.

Example 4

Fabrication of Integrated Temperature/Analyte Transducers on Polyimide

Figure 12:
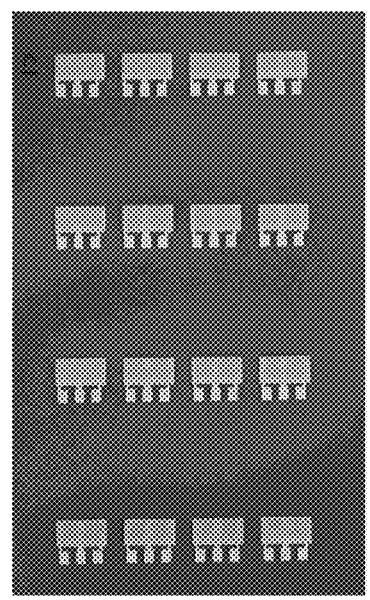
FIG. 12 is a photograph of temperature/analyte transducers on a polyimide substrate.

A sheet of integrated temperature/analyte transducers was fabricated using the same conditions as in Example 3, except a polyimide sheet (Dupont, USA) was used as a substrate. FIG. 12 shows the resulting sheet of transducers.

Example 5

Fabrication of Comparative Integrated Temperature and Humidity Transducer

An integrated temperature and humidity transducer was synthesized as relatively large transducer (about 1.5 cm$^2$) using printed electronic techniques. Electrodes were screen-printed on a polyethylene terephthalate (PET) substrate from Tekra using a nano-silver conductive ink (AG-800 from Conductive Compounds), and were cured at 110° C. for 10 minutes in a conveyer belt oven. The sensing element used was coated using the material from Example 2 and was deposited between the electrodes by spray-coating across the two electrodes at a thickness of 50 nm. Finally, DuPont 5036 polymeric encapsulation material was screen printed on the top of CNT sensing element over the temperature electrodes.

Example 6

Fabrication of Discrete Temperature Transducers

Figure 13:
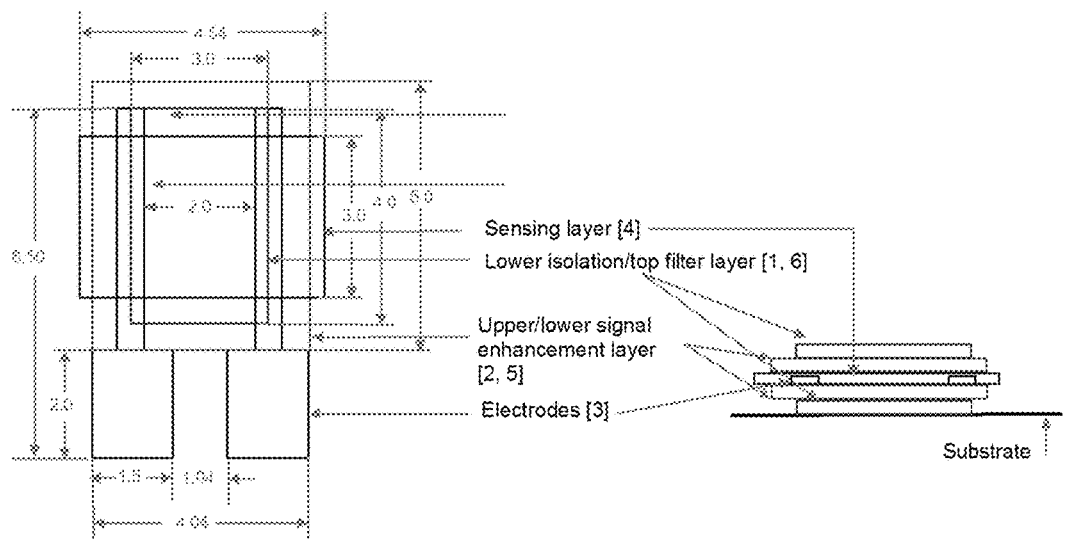
FIG. 13 is a top and side view of the simple transducer structure of Example 6.
Figure 14:
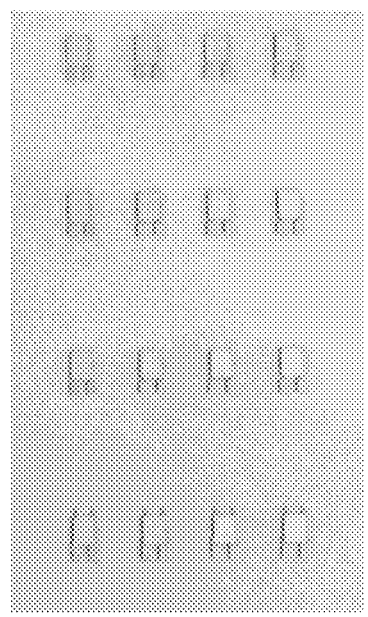
FIG. 14 is a photograph of discrete temperature transducers on a PET substrate.

Discrete temperature transducers were fabricated using the same printing parameters as in Example 3. In this design, only two electrodes were printed, and the humidity electrode was absent. The structure of the transducers is shown in FIG. 13. FIG. 14 shows the resulting sheet of transducers.

Example 7

Configuration of Transducer Testing Equipment

Figure 15:
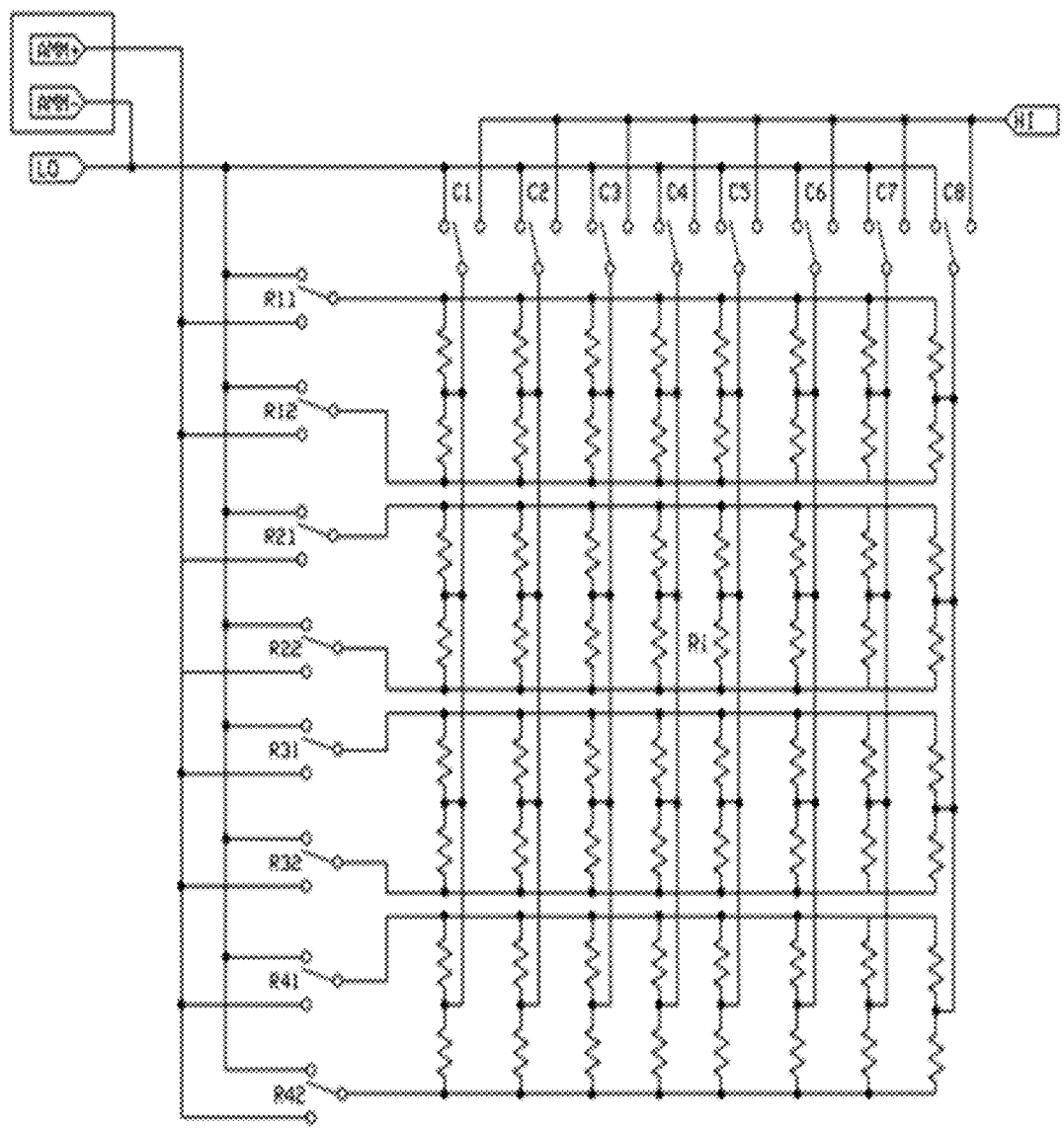
FIG. 15 is schematic showing the array operation of a scanner system measuring current with applied V to one device under test ("DUT")

The transducers were tested under controlled relative humidity and temperature inside an environmental chamber (Espec BTL-433 model), using a custom-made scanner system. The scanner board system contained a scanner board, with 96 spring-loaded pogo pins, and a clamp system, in order to electrically connect 32 integrated transducers under test to the electronics of the system for voltage supply and current/voltage output measurements. The scanner also contained four calibrated, standard sensors (two Honeywell NIH-400 humidity sensors and two Texas Instruments LM335 temperature sensors) for measuring relative humidity and temperature inside the environmental chamber. The electronic system used a Keithley's 617 electrometer to supply voltage to the standard sensors and DUTs, and to measure the current output from the DUTs. A Keithley's 195A digital multimeter was used to measure the voltage output from the standard sensors. The scanner box utilized a scanner relay board, a scanner controller, and a multiplexer to test 32 integrated temperature/analyte transducers simultaneously. For the test, each DUT was positively biased while all other devices were forced to zero to eliminate leakage current. A schematic of a section of the circuit illustrating the array operation measuring current with applied voltage of one DUT is shown in FIG. 15. The data acquisition was performed using the Lab View 2011 program. The scanner system supplied voltage to one DUT at a time. The settling time for acquiring data was set to 1 second while the data acquisition cycle was 15 minutes long.

The circuit shown in FIG. 15 is used to measure each of the resistances in the matrix by selecting one of the row (R11-R42) relays and one of column (C1-C8) relays. For example, the resistor Ri can be measured by closing relay C5 and relay R22. In closing C5 and R22, all the resistors in column 5 are connected at one end to the power supply HI terminal. All of the other resistors in all the other columns have both ends either connected to the power supply LO terminal (through the closed contacts of the relays) or the ammeter HI+ terminal which is at a virtual LO voltage (along row R22). Since all these resistors have no voltage across them and therefore no current flowing through them, the only current that can flow from the power supply flows through the resistors in column 5. But the only current that flows through the ammeter is current that flows along row 22. Since all other resistors except Ri are connected to columns other than 5 and have no current flowing through them, the current measured by the electronic ammeter is just the current that flows through Ri. The resistance of Ri is equal to the power supply voltage divided by the current measured by the electronic ammeter.

Figure 16:
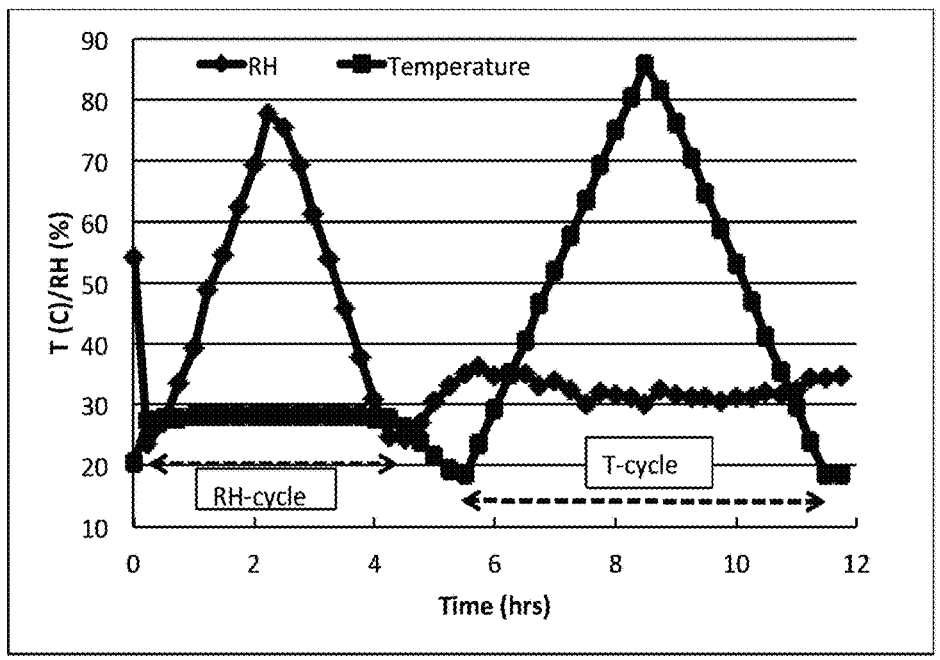
FIG. 16 is a graph showing the average relative humidity and temperature profiles inside the environmental chamber.

For hysteresis and accuracy tests of temperature/analyte transducers, the relative humidity inside the chamber was ramped from 25% to 80%, and then back to 25% at a fixed temperature (25° C.). For temperature transducer hysteresis and accuracy testing, the temperature was ramped from 20° C. to 90° C. and back to 20° C. while keeping relative humidity fixed at 35%. For each test, the output current from each transducer was measured at a fixed voltage of 0.5 V. The four standard calibrated sensors were used for measuring relative humidity and temperature inside the chamber. The relative humidity and temperature profiles of the chamber, recorded by the calibrated standard sensors, are shown in FIG. 16.

Example 8

Figure 17:
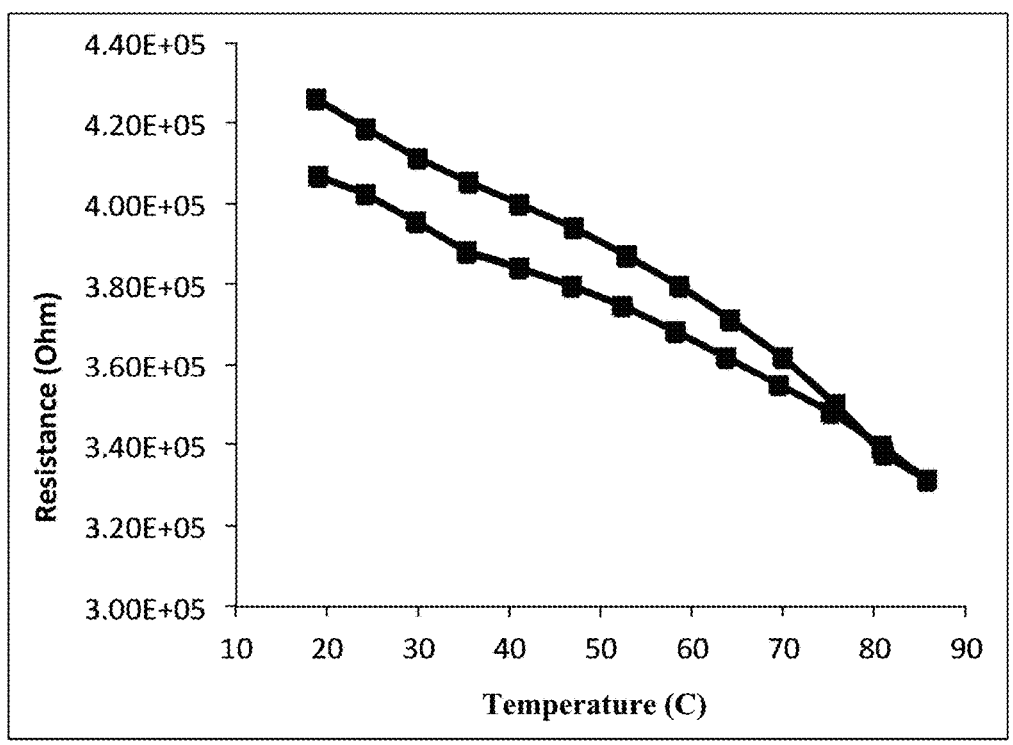
FIG. 17 is a hysteresis graph of the temperature transducer from Example 5.
Figure 18:
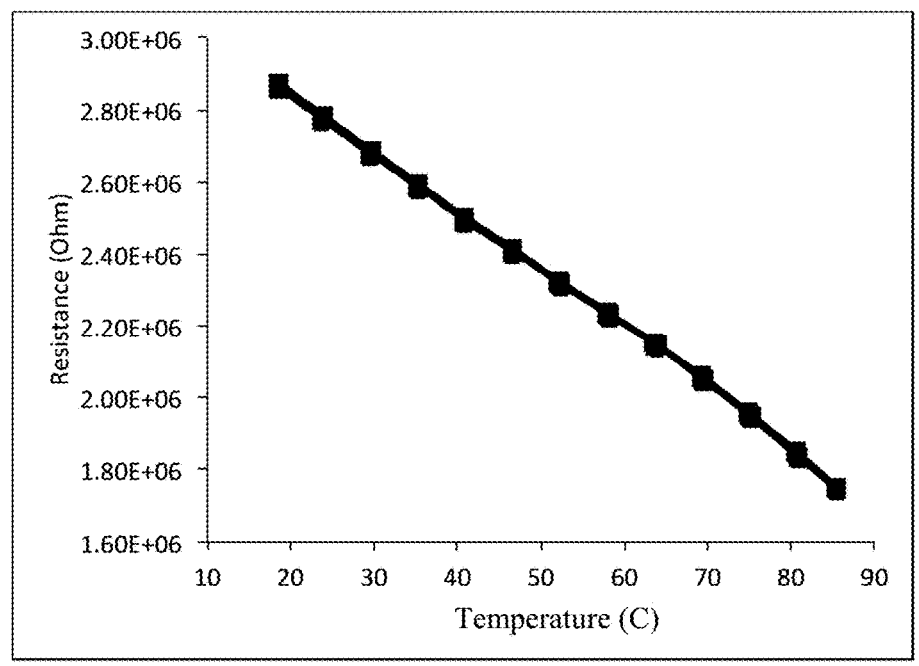
FIG. 18 is a hysteresis graph of temperature transducer from Example 3.

Temperature Hysteresis and Accuracy of Carbon Nanotube-based Temperature Transducers Hysteresis testing of the transducers fabricated in Examples 3 and 5 was performed by placing the transducers in the testing equipment described in Example 7. The temperature was cycled from 20° C. to 90° C. to 20° C. as described in Example 7, and the current output from the sensors was recorded at a fixed applied voltage of 0.5 V. A graph of resistance output vs. temperature was plotted, and a best-fit line was drawn. Using slope and y-intercept values of the best-fit line, each resistance value at each temperature recorded by the calibrated temperature sensors was converted into the calculated temperature values. The deviation of each calculated temperature from the actual temperature during the forward and reverse temperature cycles was calculated, and the temperature difference for each recorded temperature for the forward and reverse temperature cycles were added together. The maximum deviation of the calculated temperature from the actual temperature for the whole range was the hysteresis value for that device. The hysteresis of the transducer from Example 5, which did not use the signal enhancement layer or isolation layer, was approximately 16° C. and is shown in FIG. 17. The hysteresis of the transducer from Example 3 was greatly improved with the addition of the isolation and filter layer, and was about 2° C., as shown in FIG. 18.

Figure 19:
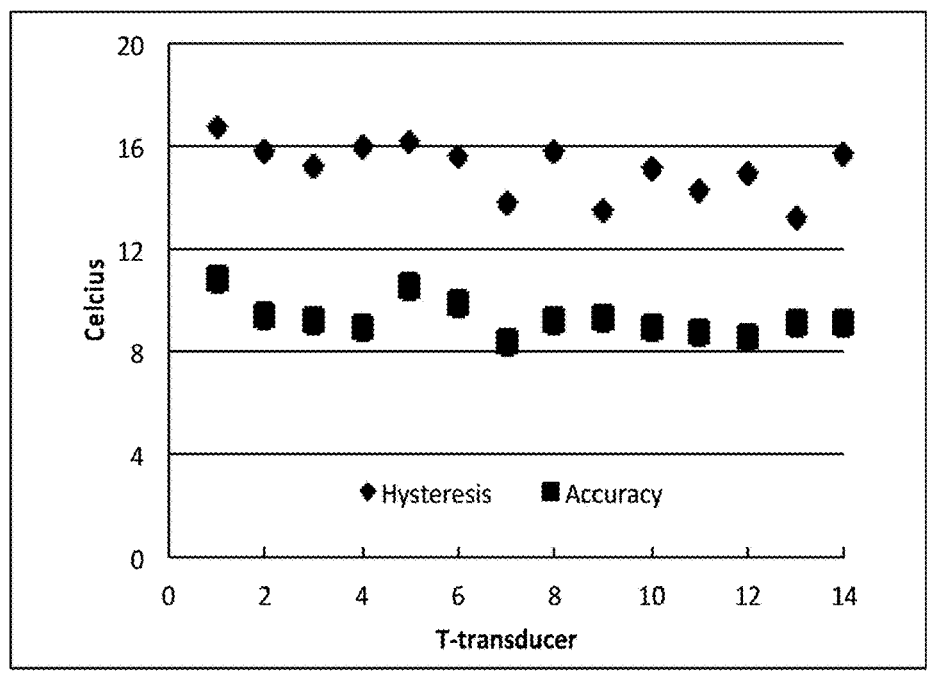
FIG. 19 is a graph showing accuracy and hysteresis of 14 temperature transducers from Example 5.
Figure 20:
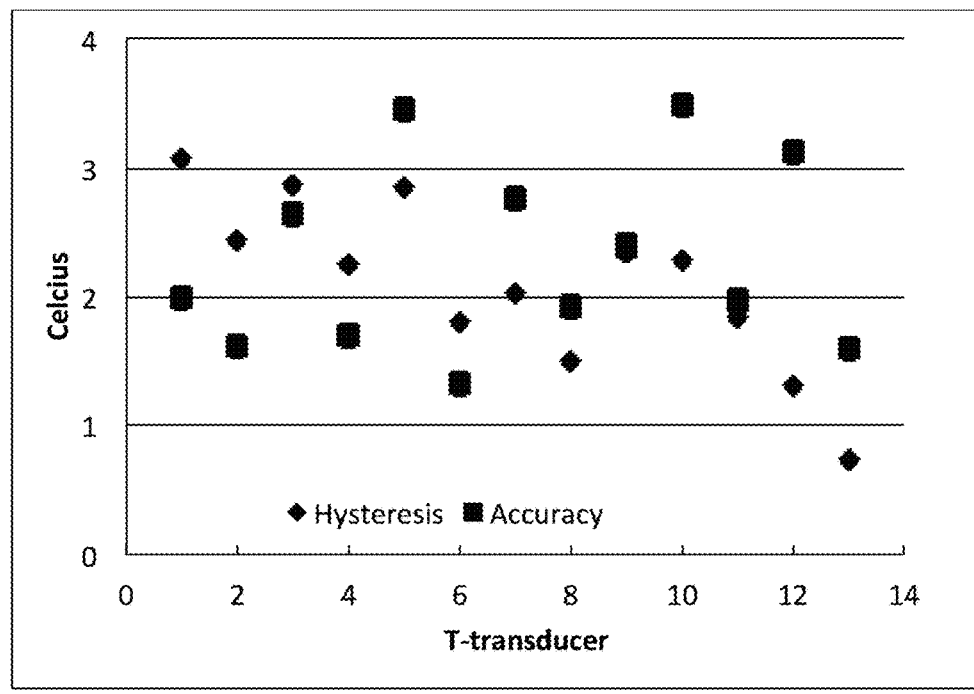
FIG. 20 is a graph showing accuracy and hysteresis of 13 temperature transducers from Example 4.

The accuracy of each temperature transducer was also calculated during the process described above by finding the difference between the calculated and actual temperature at each recorded temperature. The largest difference was the accuracy of the device. The accuracy of the sheet of transducers from Example 5 is shown in FIG. 19. The accuracy of a sheet of transducers from Example 3 was greatly improved and is shown in FIG. 20.

Example 9

Humidity Hysteresis and Accuracy of Carbon Nanotube-based Humidity Transducers

Figure 21:
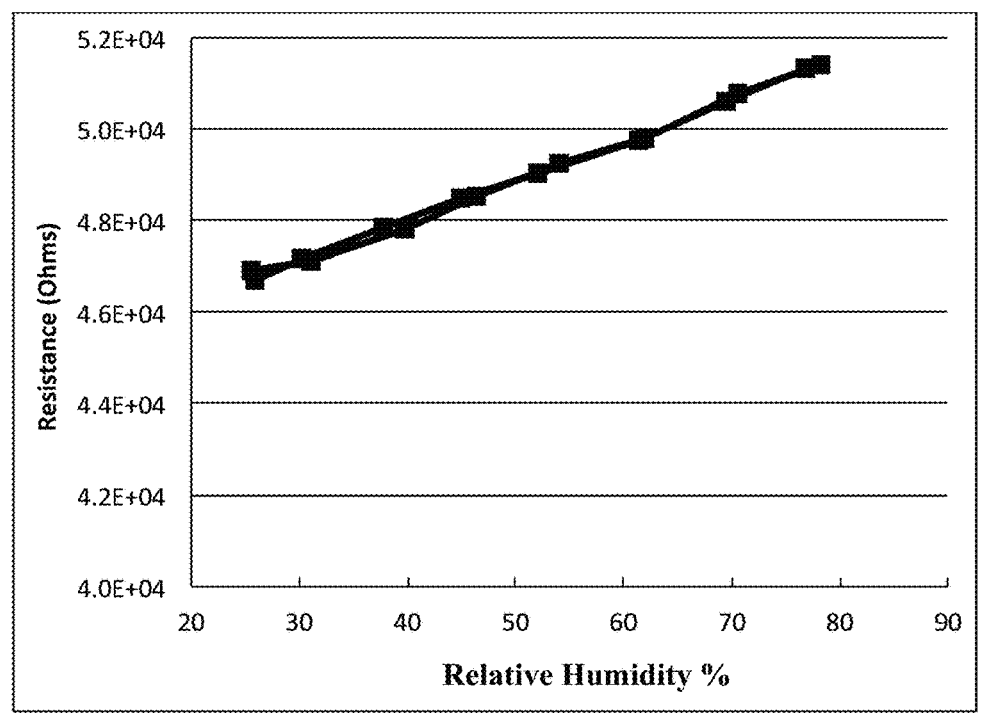
FIG. 21 is a hysteresis graph of the humidity transducer from Example 5.
Figure 22:
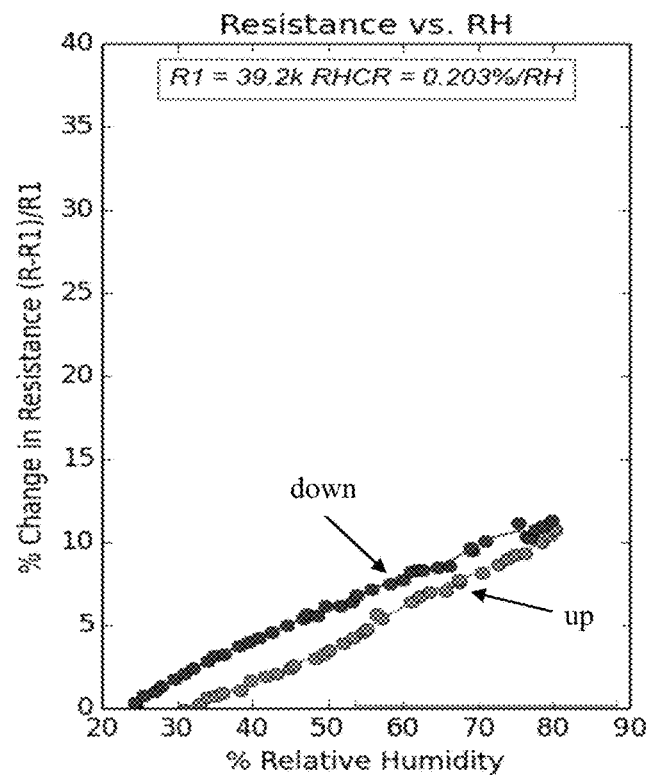
FIG. 22 is a hysteresis graph of the humidity transducer from Example 3.

Hysteresis testing of the transducers fabricated in Examples 3 and 5 was performed by placing the transducers in the testing equipment of Example 7. The relative humidity inside the chamber was ramped from 25% to 80%, and then back to 25% at a fixed temperature (25° C.) as shown in Example 7 and the current output from the sensors was recorded at a fixed applied voltage of 0.5 V. A graph of resistance output vs. relative humidity was plotted, and a best-fit line was drawn. Using slope and y-intercept values of the best-fit line, each resistance value at each humidity point recorded by the calibrated humidity sensors was converted into the calculated humidity values. The deviation of each calculated relative humidity from the actual relative humidity during the forward and reverse humidity cycles was calculated, and the humidity difference for each recorded humidity for the forward and reverse humidity cycles were added together. The maximum deviation of the calculated humidity from the actual humidity for the whole range was the hysteresis value for that device. The hysteresis of the transducer from Example 5, which did not use the signal enhancement layer or isolation layer is shown in FIG. 21. The hysteresis of the transducer from Example 3 is shown in FIG. 22.

Figure 23:
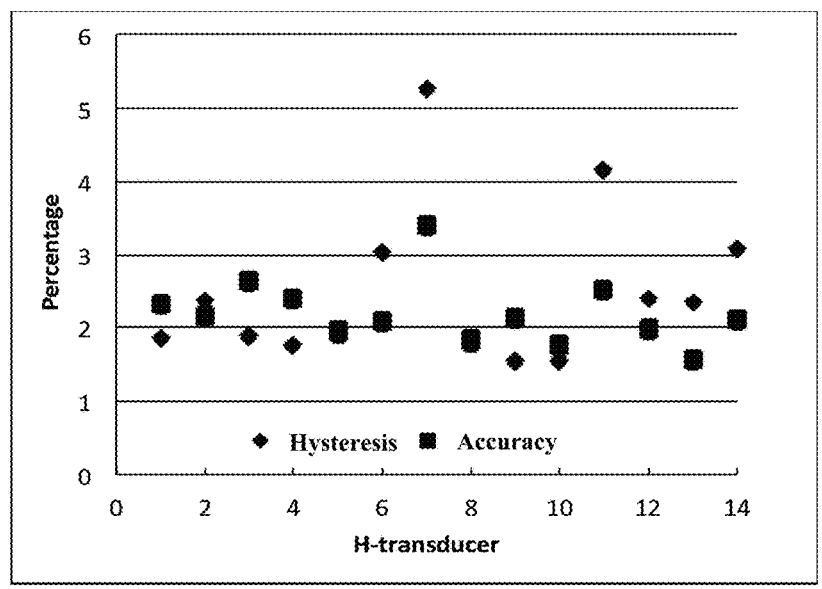
FIG. 23 is a graph of the accuracy and hysteresis of 14 humidity transducers from Example 5.

The accuracy of each humidity transducer was also calculated during the process described above by finding the difference between the calculated and actual humidities at each recorded humidity. The largest difference was the accuracy of the device. The accuracy of a sheet of transducers from Example 5 is shown in FIG. 23.

Example 10

Device Stability Over Time

Figure 24:
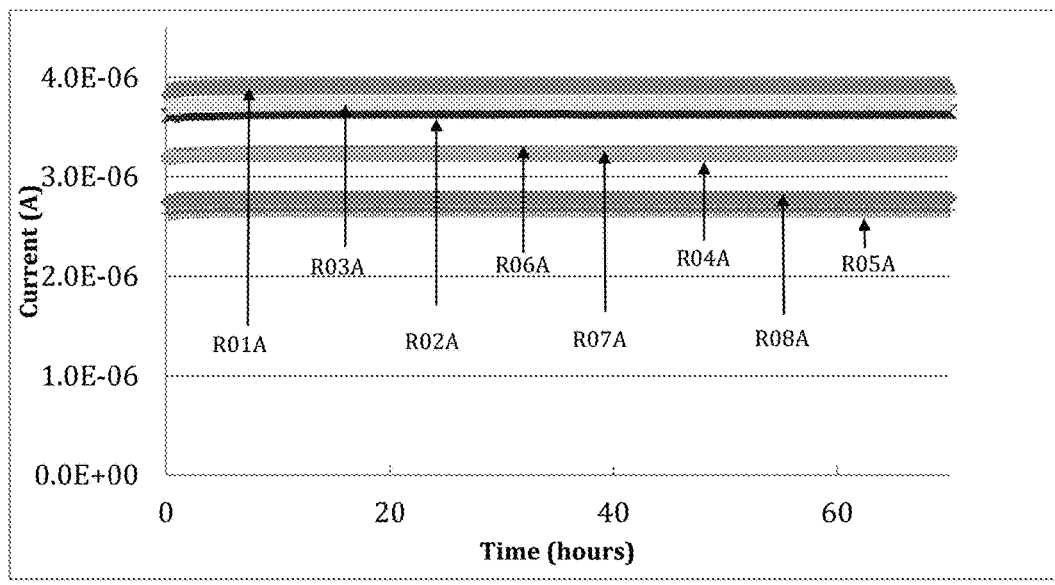
FIG. 24 is a graph of current vs. time of temperature transducers at fixed temperature and RH.
Figure 25:
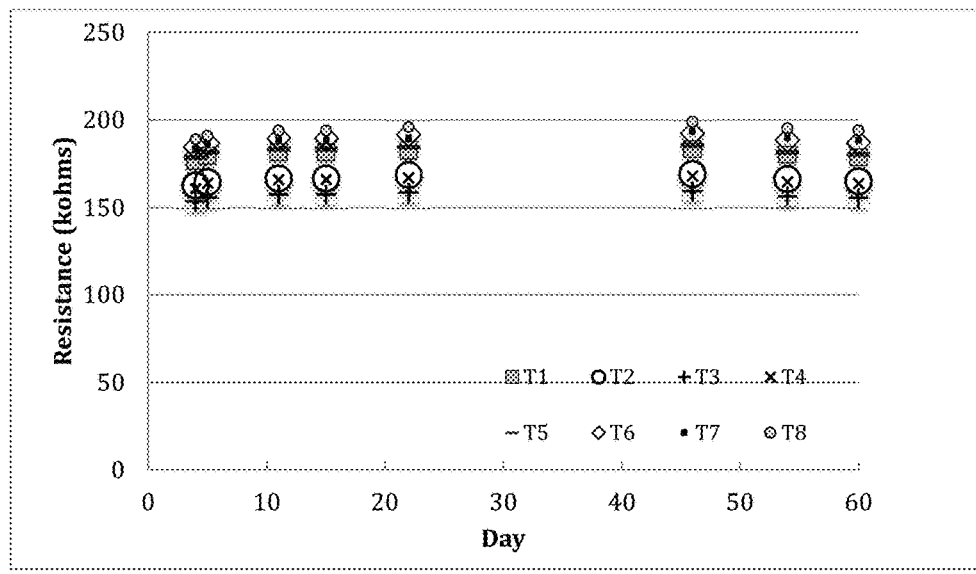
FIG. 25 is a graph of resistance vs. time of 8 temperature transducers at room conditions for 60 days.

The temperature transducers from Example 5 were tested in environmental chamber at a fixed temperature and relative humidity (25° C./50% RH) for an extended period of time in order to test the device stability over time. FIG. 24 shows the output current of 8 representative temperature transducers in the environmental chamber for a period of 72 hours. FIG. 25 shows the resistance output of 8 temperature transducers, as measured by a digital multimeter at ambient room conditions for 60 days. As shown, the devices show extremely stable performance over time.

Figure 26:
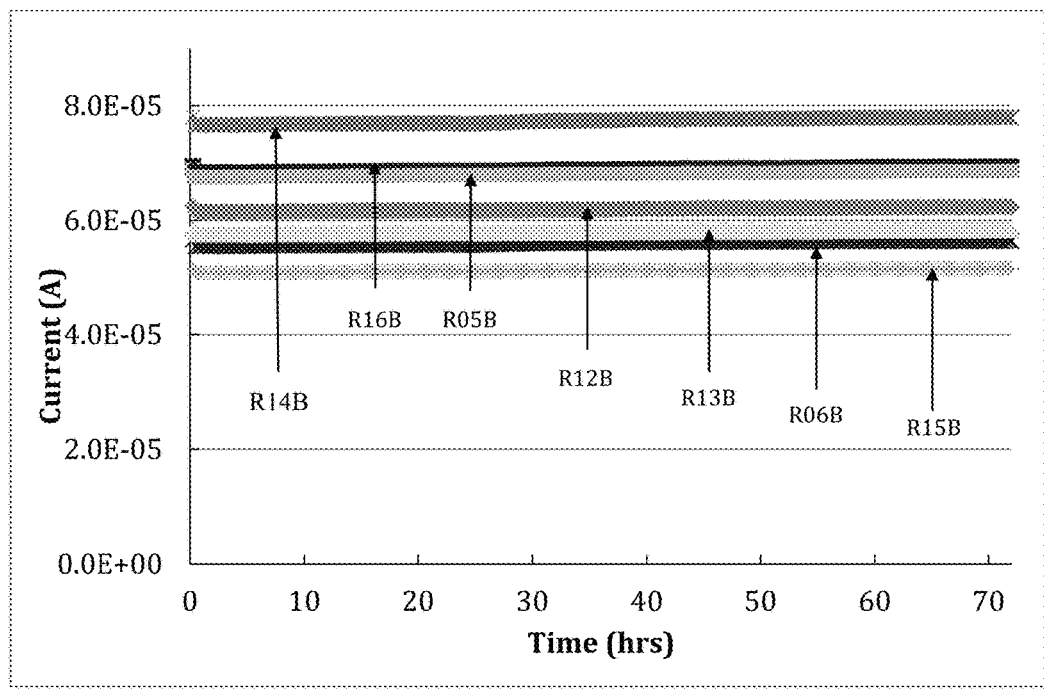
FIG. 26 is a graph of current vs. time of humidity transducers at fixed temperature and RH.
Figure 27:
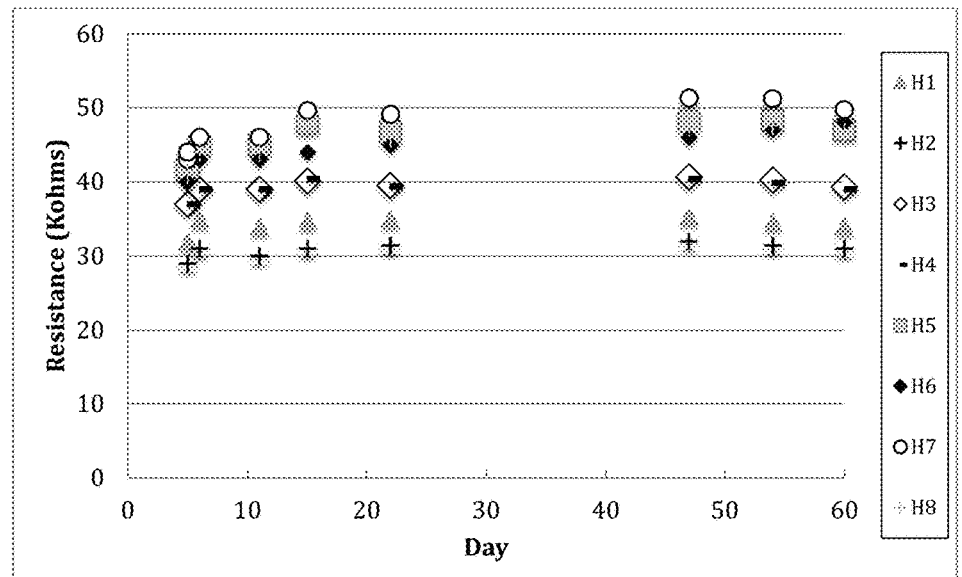
FIG. 27 is a graph of resistance vs. time of 8 humidity transducers at room conditions for 60 days.

The humidity transducers from Example 5 were tested in environmental chamber at a fixed temperature and relative humidity (25° C./50% RH) for an extended period of time in order to test the device stability over time. FIG. 26 shows the output current of 8 representative humidity transducers in the environmental chamber for a period of 72 hours. FIG. 27 shows the resistance output of 8 humidity transducers, as measured by a digital multimeter at ambient room conditions for 60 days. As shown, the devices show extremely stable performance over time.

Example 11

Speed Measurement of an Integrated Temperature and Analyte Transducer

Figure 28:
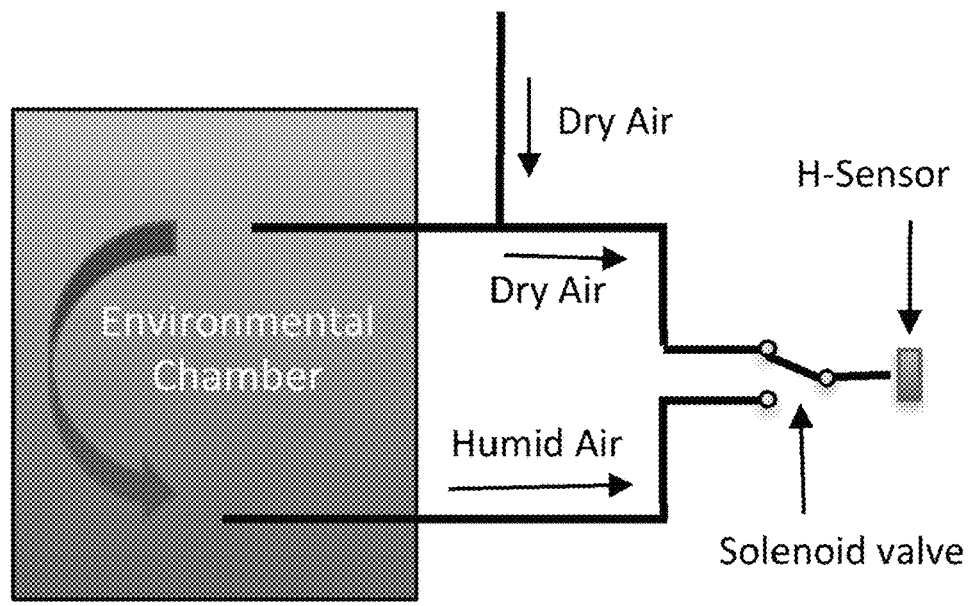
FIG. 28 is a schematic showing an experimental setup used to determine response and recovery time of an analyte transducer.

The transducer fabricated in Example 5 was tested for its response and recovery time to the introduction of humid air. An experimental set-up for measuring the response and recovery time is shown in FIG. 28. Dry and humid (30% relative humidity) air was introduced as 1-second pulses to the transducer, using a solenoid valve (Ingersoll-Rand P251SS120-A-G). The response time (1/e) of the transducer when the humid air was introduced to it, and the recovery time when the humid air was replaced by dry air after 1 second is shown in FIG. 8. The response time was <10 milliseconds and the recovery time was about 40 milliseconds.

Example 12

Speed Measurement of an Integrated Temperature Transducer

Figure 29:
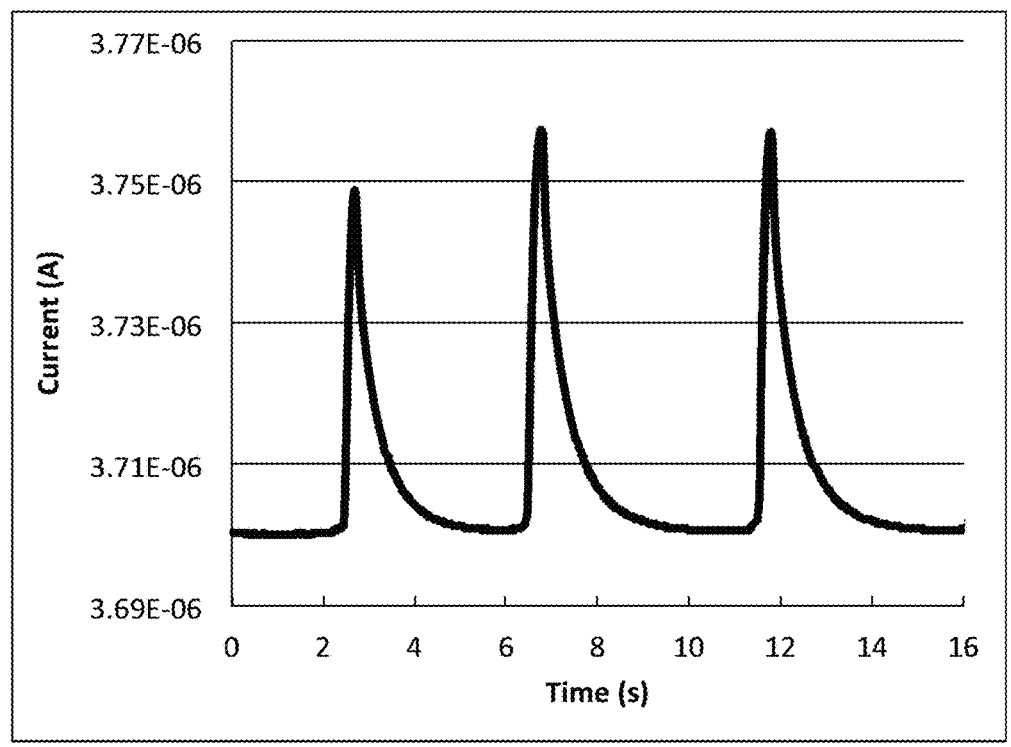
FIG. 29 is a graph showing the response and recovery times of a temperature transducer to heat from a finger.

To evaluate the sensitivity and speed of the transducer from Example 5 to heat change, the transducer was touched with a finger and then released, and the current output data was recorded in real time using a Keithley's 4200-SCS semiconductor analyzer. The response of the transducer to heat from a human finger is shown in FIG. 29. As shown, the temperature transducer responds very quickly to even very small heat from the finger when touched, and recovers very quickly when released. The temperature transducer has a response time of <50 milliseconds and recovery time of <150 milliseconds.

Example 13

Comparative Thin-Film Temperature Transducer Using an Organic Polymer

Figure 30:
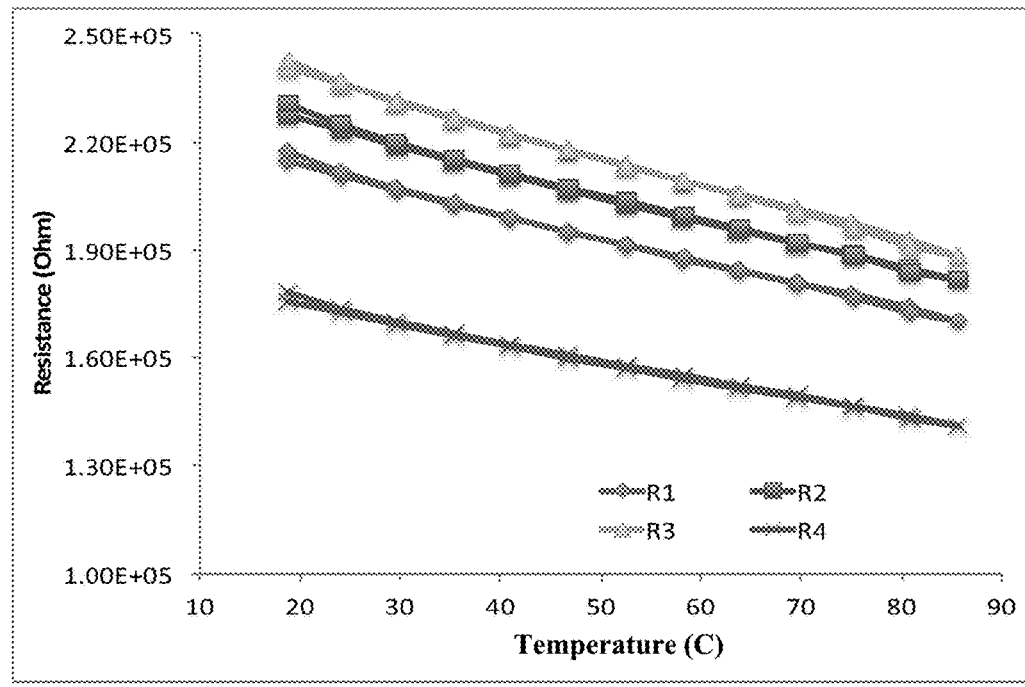
FIG. 30 is a graph of the response of a PEDOT:PSS-based temperature transducer.
Figure 31:
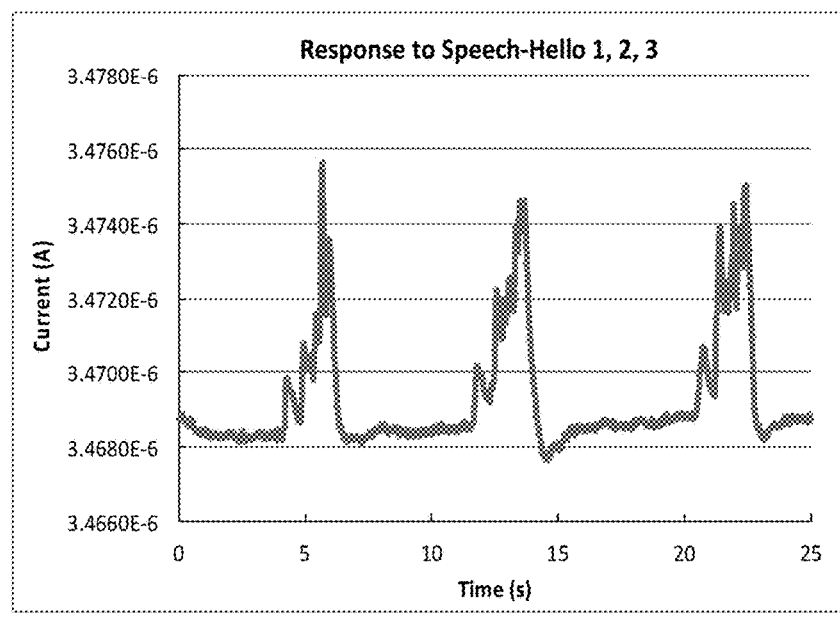
FIG. 31 is a graph of the response to heat fluctuation during speaking "Hello one, two, three"

A thin-film temperature transducer was fabricated as in Example 5, except that a 10-nm layer of conductive polymer, PEDOT:PSS (Sigma Aldrich, Product number 655201), was utilized in place of the CNT ink as the active sensing layer. FIG. 30 shows the response of four representative PEDOT:PSS-based temperature transducers during forward and backward temperature cycles in the environmental chamber of Example 7. The transducers have hysteresis of less than 4° C. The transducers also possess ultrahigh speed, with a response time of less than 50 milliseconds. FIG. 31 shows the response of the polymer-based temperature transducer to heat fluctuation while held 1.5 inches from a person speaking "Hello one, two, three."

Example 14

Thin-Film Temperature Transducer Using an Organic Polymer

Figure 32:
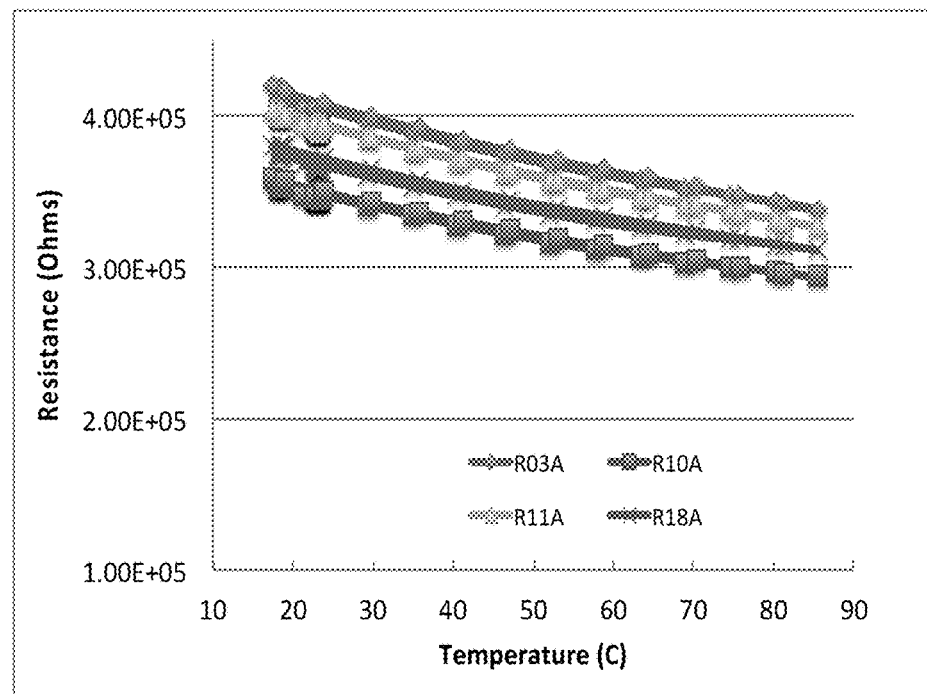
FIG. 32 is a graph of the response of a PEDOT:PSS-based temperature transducer.

A thin-film temperature transducer was fabricated as in Example 3, except that a 10-nm layer of conductive polymer, PEDOT:PSS (Sigma Aldrich, Product number 655201), was utilized in place of the CNT ink as the active sensing layer. FIG. 32 shows the response of four representative PEDOT:PSS-based temperature transducers during forward and backward temperature cycles in the environmental chamber of Example 7.

Example 15

Low-Power Operation of Integrated Transducer

Figure 33:
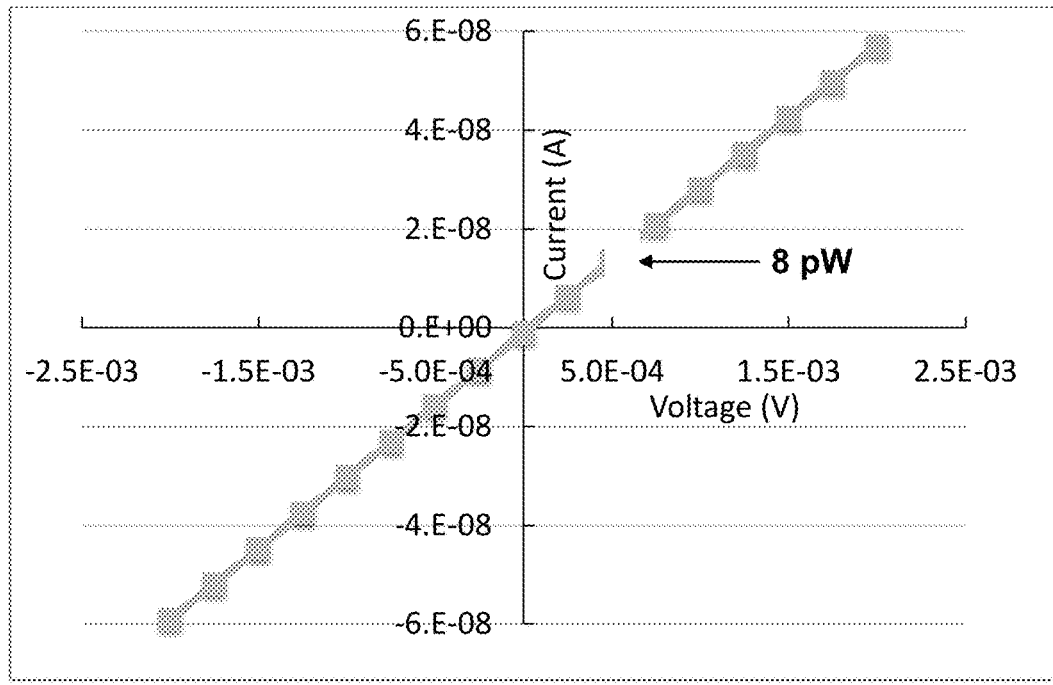
FIG. 33 is a graph showing the low voltage, I-V behavior of a temperature/analyte sensor.
Figure 34:
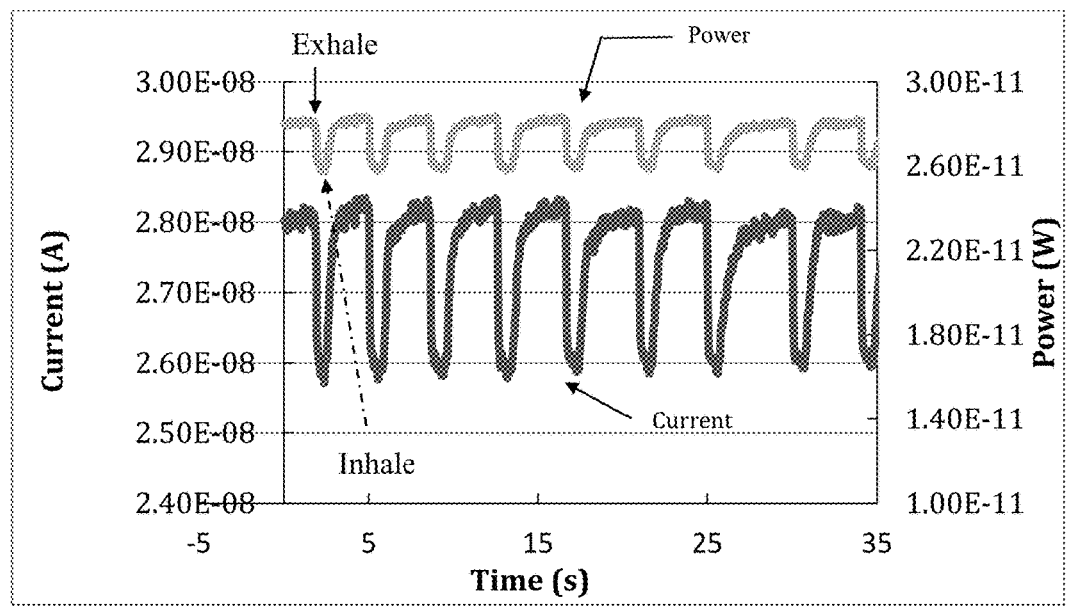
FIG. 34 is a graph depicting low-power (<30 pW) operation of a temperature/analyte transducer in response to human breathing.

The integrated temperature/analyte transducers can operate at extremely low power (few pW), making them suitable for low-battery-drain operation and long-term process/environmental monitoring applications. The I-V behavior of a temperature/analyte transducer fabricated in Example 5 in the voltage range of −2.5 mV, +2.5 mV, using Keithley's SCS4200 semiconductor analyzer, is shown in FIG. 33. As shown, they demonstrate linear behavior down to extremely low voltages. FIG. 34 shows the response of a temperature/analyte transducer, operated at 1 μV, to human breathing. The transducer consumes <30 pW of power during this breathing monitoring operation.

Example 16

Volatile Organic Compound (VOC) Vapor Detection Transducers

Figure 35:
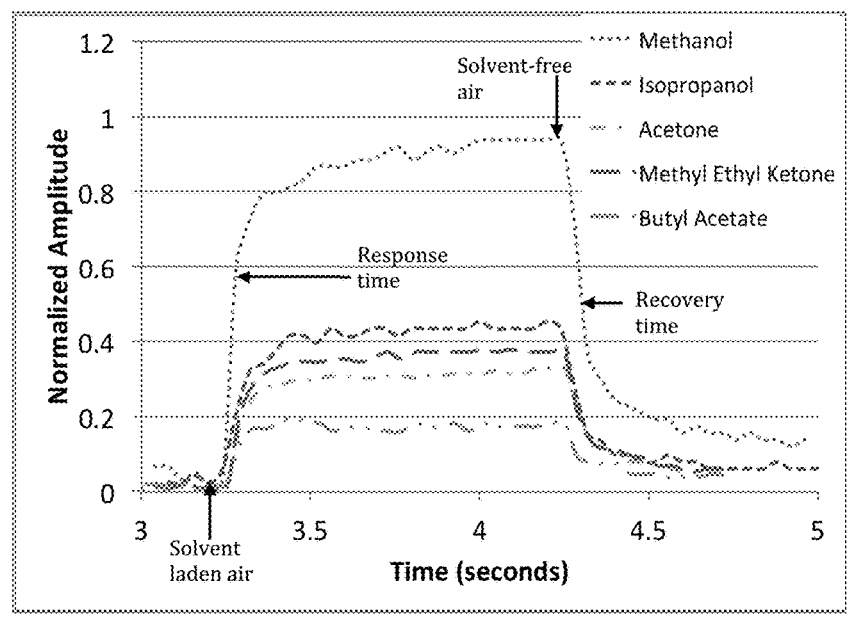
FIG. 35 is a graph showing the plot of response and recovery times to different volatile organic vapors.

Integrated temperature/analyte transducers were fabricated as in Example 5. An experimental setup for measuring response and recovery times is shown in FIG. 28, where solvent vapors were introduced to the air stream by blowing the dry air over a pool of solvent instead of humidity. The solvent-laden air was passed through a glass frit before reaching the transducer. For response and recovery time testing, the sensor was purged with dry air for 1 minute, then line was purged with solvent-laden air for 5 seconds, and then a 1-second pulse of solvent-laden air was introduced to the transducer using the solenoid (Ingersoll-Rand P251SS120-A-G). The response time was calculated as the time between the leading edge of the pulse and the point at which the response reached 63.2% of the span between the baseline signal and the signal maxima. Similarly, the recovery time was taken as the time between the falling edge of the pulse and the point at which the response reached 63.2% of the initial baseline. Because voltage output changes exponentially, the time to reach 63.2% of the maximum output is used as industry standard to calculate response time. These transducers are sensitive not only to humidity, but also to several classes of polar volatile organics with very fast response and recovery times as shown in FIG. 35 and Table 1.

TABLE 1

| Class | Solvent | Response Time (ms) | Recovery Time (ms) |
|---|---|---|---|
| Alcohol | Methanol | 16.0 | 31.6 |
|  | Isopropanol | 42.6 | 14.4 |
| Ketone | Acetone | 30.0 | 21.6 |
|  | MEK | 33.2 | 30.0 |
| Ester | Butyl Acetate | 17.2 | 75.6 |

Example 17

Speech Recognition with the Humidity Transducer

The integrated temperature/humidity transducer from Example 5 was tested in its effectiveness for acquiring a speech-generated relative humidity (RH) signal by varying the distance between the mouth and the sensor, as well as testing indoors and outdoors. Indoors, the sensor gave a clear RH signal from a person speaking "1-2-3" at a distance of over 20 cm from the transducer (lab temperature=23° C., RH=55%). The signal could be amplified with the use of proper electronics and amplifier so that the sensor device for speech recognition can be used for even longer distance.

The same sensor was tested in an open air (wind speed approximately 9 miles/hr) outdoors, with the sensor at a 5-cm distance from the mouth. There was a clear speech-generated RH signal when there was no to slight breeze. However, there was no RH signal during a relatively strong breeze.

Example 18

Temperature Hysteresis and Accuracy of Carbon Nanotube-based Temperature Transducers Temperature transducers were fabricated as in Example 6, except that the active layer used an ink containing Zeon CNTs with an optical density of 2. The active layer was spray coated in three layers to form the active layer. The temperature transducers were tested as in Example 7.

Figure 36:
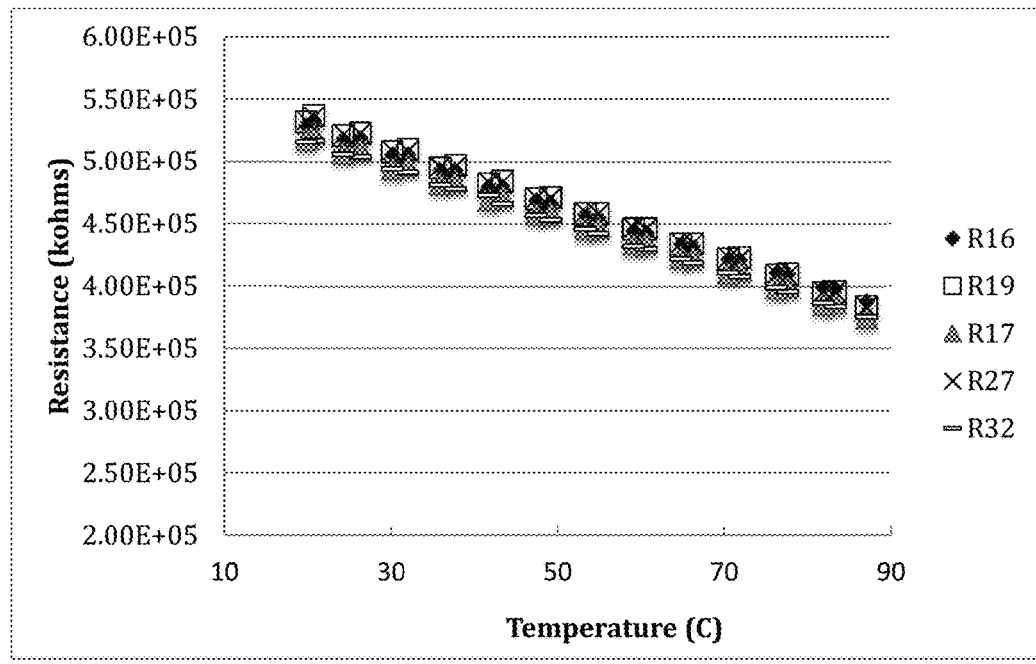
FIG. 36 is a hysteresis graph of Zeon CNT-based temperature transducers.
Figure 37:
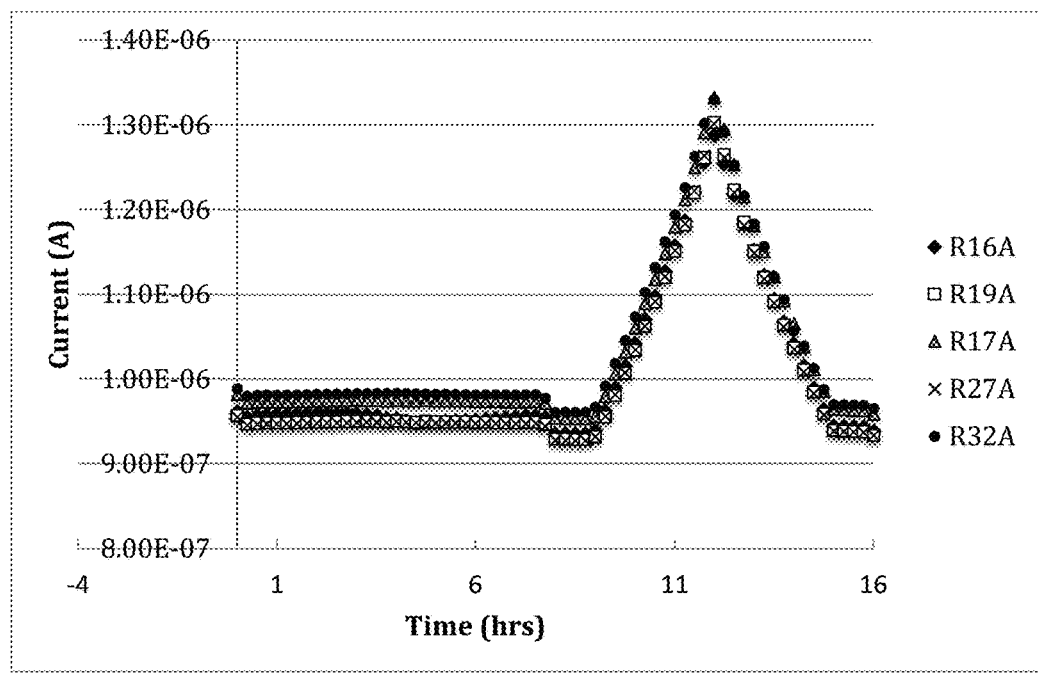
FIG. 37 is a graph showing the response of the sensors to RH change and T-change.

The hysteresis and accuracy of the all sensors were below 3° C. and 2.5° C. respectively, as shown in FIG. 36. The temperature coefficient of resistance (% change in resistance per degree temperature change) was about 0.55%/° C. As shown in FIG. 37, the sensors do not respond to RH change (1.25 hr to 7.25 hr) at all, but show response to T-change (9 hr to 15 hr).

Example 19

Preparation of Semiconducting Carbon Nanotube Ink 3

In this procedure, 20 milligrams of SWeNT SG65 raw CNT material was mixed with 200 milliliters of 0.5% sodium dodecylbenzenesulfonate (SDBS) (by weight) in deionized water. The slurry was dispersed using a microfluidizer (model: M10Y, column size: 87 μm) for 20 minutes. The resulting dispersion was centrifuged for 30 minutes at 22.5 rpm. The final OD of the ink was 1.90.

Example 20

Temperature Hysteresis and Accuracy of Semiconducting Carbon Nanotube-based Temperature Transducers Temperature transducers were fabricated as in Example 6, except that the active layer used the ink from Example 19. The active layer was spray coated onto the transducer, and the surfactant was removed from the active layer by an isopropanol dip wash followed by a deionized water dip wash. The temperature transducers were tested as in Example 7.

Figure 38:
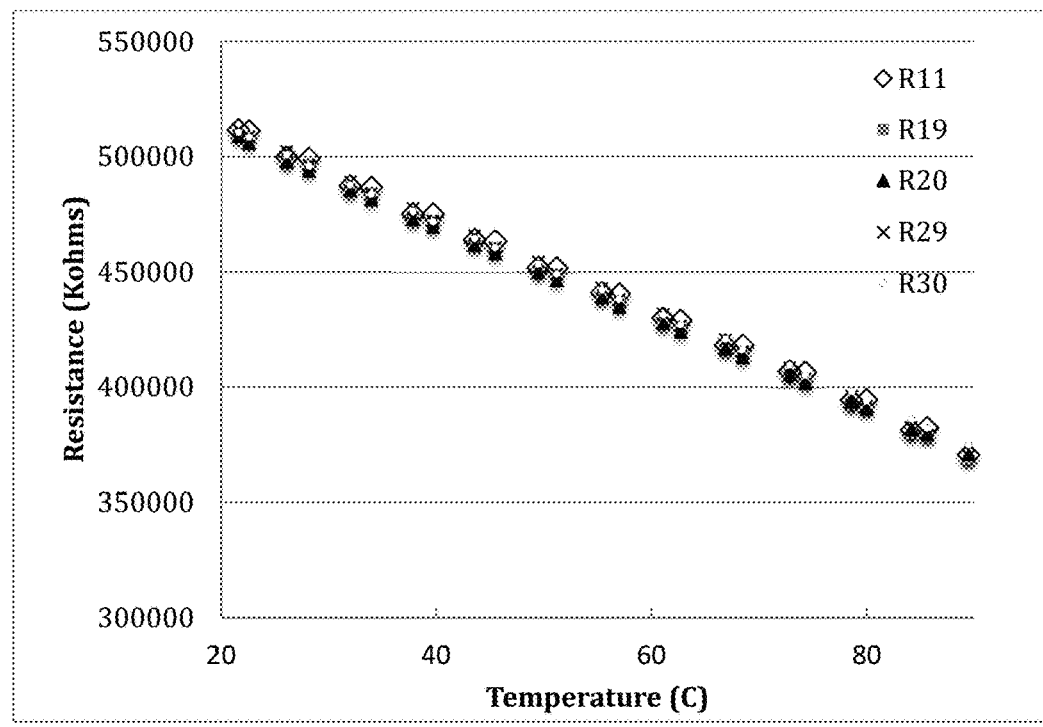
FIG. 38 is a hysteresis graph of semiconducting CNT-based temperature transducers.
Figure 39:
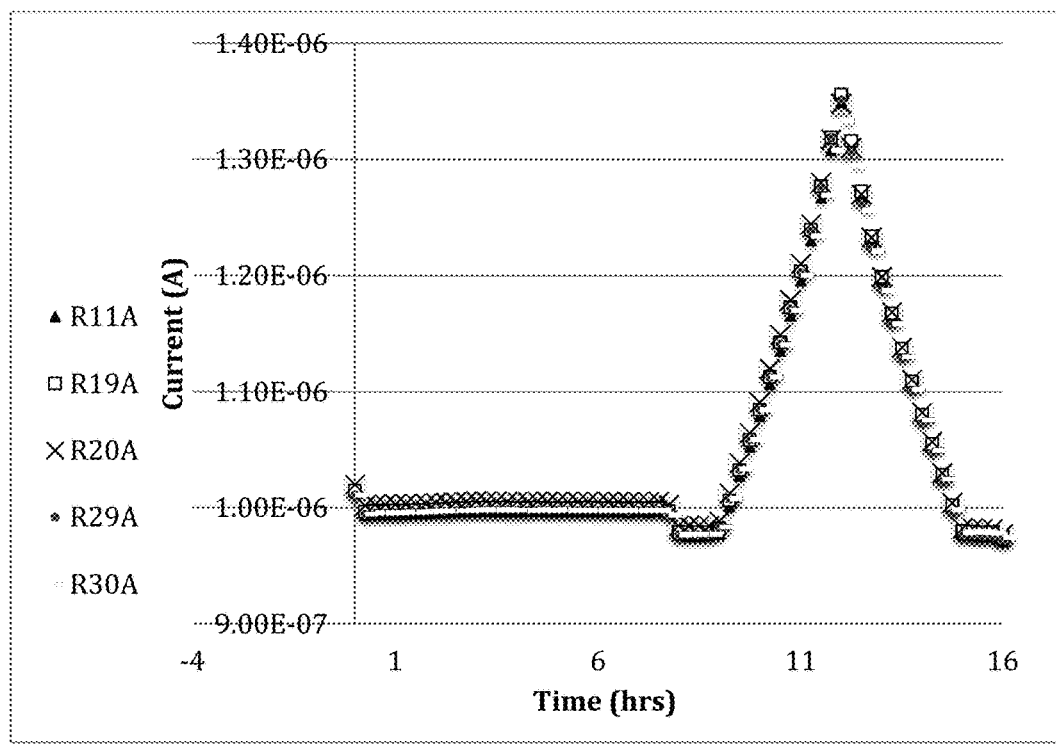
FIG. 39 is a graph showing the response of the sensors to RH change and T-change.

The hysteresis and accuracy of the all sensors were below 1.5° C., as shown in FIG. 38. The temperature coefficient of resistance was about 0.55%/° C. As shown in FIG. 39, the sensors do not respond to RH change (1.25 hr to 7.25 hr) at all, but show response to T-change (9 hr to 15 hr).

We claim:
1. A transducer comprising:
   a barrier layer having an average thickness of about 50 nm to about 50 μm;
   an active sensing layer in contact with at least two electrodes, wherein said active sensing layer has a thickness of less than about 1,000 nm and is selected from the group consisting of carbon nanotubes, carbon nanotube fabrics, amorphous carbon films, graphite, graphene, pyrolytic carbon, carbon fibers, carbon black, silicon, conductive polymers, fullerenes carbon soot, and composites and mixtures of the foregoing; and
   a dielectric layer between said active and barrier layers and having first and second sides, said at least two electrodes both being adjacent said dielectric layer second side, said transducer being a resistive transducer.

2. The transducer of claim 1, wherein said barrier layer comprising a material selected from the group consisting of metals, metal oxides, metal nitrides, semiconductors, glass, organic polymers, and mixtures of the foregoing.

3. The transducer of claim 1, wherein said dielectric layer comprises a material selected from the group consisting of non-conductive polymers, non-conductive photoresists, non-conductive ceramics, non-conductive metal nitrides, non-conductive metal oxides, non-conductive metal composites, and mixtures thereof.

4. The transducer of claim 3, further comprising a signal enhancement layer against said active sensing layer second side.

5. The transducer of claim 4, wherein said signal enhancement layer comprises a material selected from the group consisting of non-conductive polymers, non-conductive photoresists, non-conductive ceramics, non-conductive metal nitrides, non-conductive metal oxides, non-conductive metal composites, and mixtures thereof.

6. The transducer of claim 1, said active sensing layer having first and second sides, with said active sensing layer first side being against said dielectric layer second side.

7. The transducer of claim 1, wherein said barrier layer has first and second sides, said dielectric layer being adjacent said barrier layer second side, and further comprising a substrate against said barrier layer first side.

8. The transducer of claim 7, wherein said substrate is selected from the group consisting of metals, metal oxides, metal nitrides, semiconductors, glass, paper, organic polymers, and mixtures of the foregoing.

9. The transducer of claim 1, wherein;
said barrier layer comprises a material selected from the group consisting of metals, metal oxides, metal nitrides, semiconductors, glass, organic polymers, and mixtures of the foregoing; and
said dielectric layer comprises a material selected from the group consisting of non-conductive polymers, non-conductive photoresists, non-conductive ceramics, non-condutive metal nitrides, non-conductive metal oxides, non-conductive metal composites, and mixtures thereof.

10. The transducer of claim 1, said transducer having a response time of less than about 50 msec and a fall time of less than about 100 msec under atmospheric conditions.

11. A sensor comprising a transducer according to claim 1.

12. The sensor of claim 11, further comprising a controller unit operably coupled with said transducer.

13. The sensor of claim 11, said transducer having a response time of less than about 50 msec and a fall time of less than about 100 msec under atmospheric conditions.

14. The sensor of claim 11, said controller unit being operably coupled with said transducer so that the change in resistance encountered by said transducer upon exposure to an analyte can be detected and analyzed by said controller unit.

15. The sensor of claim 12, wherein:
said barrier layer comprises a material selected from the group consisting of metals, metal oxides, metal nitrides, semiconductors, glass, organic polymers, and mixtures of the foregoing; and
said dielectric layer comprises a material selected from the group consisting of non-conductive polymers, non-conductive photoresists, non-conductive ceramics, non-conductive metal nitrides, non-conductive metal oxides, non-conductive metal composites, and mixtures thereof.

16. A method of detecting existence of a condition, said method comprising:
introducing a transducer into an environment where said analyte might be present, said transducer comprising:
a barrier layer having an average thickness of about 50 nm to about 50 µm;
an active sensing layer in contact with at least two electrodes, wherein said active sensing layer has a thickness of less than about 1,000 nm and is selected from the group consisting of carbon nanotubes, carbon nanotube fabrics, amorphous carbon films, graphite, graphene, pyrolytic carbon, carbon fibers, carbon black, silicon, conductive polymers, fullerenes carbon soot, and composites and mixtures of the foregoing; and
a dielectric layer between said active and barrier layers and having first and second sides, said at least two electrodes both being adjacent said dielectric layer second side; and
observing whether said transducer indicates the existence of the condition, wherein said existence is indicated by a change in resistance.

17. The method of claim 16, wherein said condition is one selected from the group consisting of presence of an analyte, change in temperature, or both.

18. The method of claim 17, wherein said analyte is selected from the group consisting of humidity, gas, airflow, VOCs, and combinations of the foregoing.

19. The method of claim 16, said transducer having a response time of less than about 50 msec and a fall time of less than about 100 msec under atmospheric conditions.

* * * * *